US006949639B1

(12) United States Patent
Hovinen et al.

(10) Patent No.: US 6,949,639 B1
(45) Date of Patent: Sep. 27, 2005

(54) OLIGONUCLEOTIDE LABELING REACTANTS AND THEIR USE

(75) Inventors: Jari Hovinen, Raisio (FI); Harri Takalo, Turku (FI)

(73) Assignee: Wallac Oy, Turku (FI)

( * ) Notice: Subject to any disclaimer, the term of this patent is extended or adjusted under 35 U.S.C. 154(b) by 512 days.

(21) Appl. No.: 09/847,384

(22) Filed: May 3, 2001

(30) Foreign Application Priority Data

May 5, 2000 (FI) ............................................. 20001046

(51) Int. Cl.[7] .............................................. C07H 19/04

(52) U.S. Cl. .................. 536/26.6; 536/25.3; 536/25.32; 536/26.1; 536/26.8; 536/27.1; 536/27.13; 536/28.1; 536/28.6

(58) Field of Search ............................. 536/25.3, 25.32, 536/26.1, 26.6, 26.8, 27.1, 27.13, 28.1, 28.6

(56) References Cited

U.S. PATENT DOCUMENTS

| 4,837,312 A | 6/1989 | Dervan et al. ................. 536/27 |
| 6,080,839 A | 6/2000 | Takalo et al. ................. 530/334 |

FOREIGN PATENT DOCUMENTS

| CA | 2099542 | 1/1994 | |
| EP | 0 267 996 | 5/1988 | |
| EP | 0 578 067 | 1/1994 | |
| EP | 0 967 205 | 12/1999 | |
| WO | WO 93/19078 | 9/1993 | |
| WO | WO 99/64431 | * 12/1999 | ........... C07H/19/10 |

OTHER PUBLICATIONS

Latva et al. Journal of Luminescence (1997), vol. 75, pp. 149–169.*
Kwiatkowski et al. Nucleic Acids Research, 1994, vol. 22, pp. 2604–2611.*
Sigmund et al. Nucleosides & Nucleotides, 1997, vol. 16, pp. 685–696.*
Kwiatkowski et al., "Solid–Phase Synthesis of Chelate–labelled Oligonucleotides: Application in Triple–color Ligase–mediated Gene Analysis," 22 *Nucleic Acids Res.* 2604 (1994).
Osborne et al., "Design, Synthesis, and Analysis of Disulfide Cross–Linked DNA Duplexes," 118*J. Am. Chem. Soc.* 11993 (1996).
Markiewicz et al., "Synthesis of Polyaminooligonucleotides and Their Combinatorial Libraries," 18*Nucleosides & Nucleotides* 1449 (1999).
Burmeister et al., "Synthesis of Novel Phosphoramidite Derivatives Bearing Pyrenyl and Dansyl Groups," 36 *Tertahedron Letters* 3667 (1995).

Nawrot et al., "RNA Modified Uridines VII: Chemical Synthesis and Initial Analysis of D–Loop Oligomers with Tandem Modified Uridines," 14 *Nucleosides & Nucleotides* 143 (1995).

(Continued)

*Primary Examiner*—James O. Wilson
*Assistant Examiner*—Patrick Lewis
(74) *Attorney, Agent, or Firm*—James C. Lydon

(57) ABSTRACT

The invention relates to a novel labeling reactant of formula (I) suitable for labeling an oligonucleotide

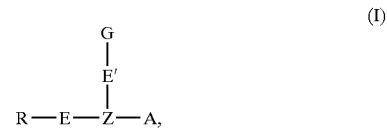

wherein:
R is a temporary protecting group. A is either a phosphorylating moiety or a solid support tethered to a bridge point Z via a linker arm E. E' is a linker arm between G and Z. G is a bivalent aromatic structure, tethered to two iminodiacetic acid ester groups N(COOR''')$_2$ or G is a structure selected from a group consisting of

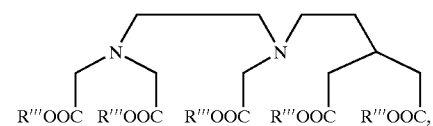

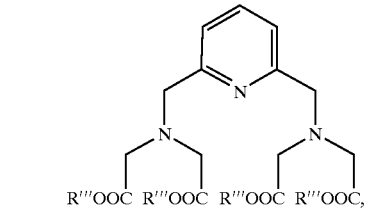

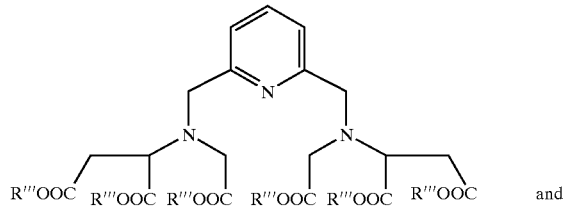

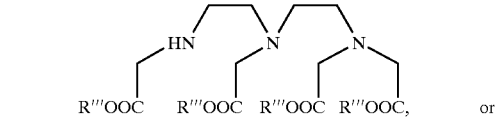

G is a protected functional group. The invention further concerns a method for direct attachment of a conjugate group to an oligonucleotide structure enabling the attachment of a desired number of these groups during chain assembly. The method comprises a Mitsonobu alkylation.

18 Claims, No Drawings

OTHER PUBLICATIONS

Sigmund et al., "A New Type of Flouscence Labeling of Nucleosides, Nucleotides and Oligonucleotides," 16 *Nucleosides & Nucleotides* 685 (1997).

Brossette et al., "Synthesis of Polyphosphorylated AZT Derivatives for the Development of Specific Enzyme Immunoassays," 64 *J. Org. Chem.* 5083 (1999).

Mukkala et al., "New Heteroaromatic Complexing Agents and Luminescence of Their Europium (III) and Terbium (III) Chelates," 75 *Helvetica Chimica Acta* 1621–1632 (1992).

Mukkala et al., "Development of Luminescent Europium (III) and Terbium (III) Chelates of 2,2':6,2"–Terpyridine Dervatives for Protein Labelling," 76 *Helvetica Chimica Acta* 1361–1378 (1993).

Mukkala et al., "The Synthesis and Luminescence Properties of Some Eu(III) and Tb(III) Chelate Labels Having 2,2':6', 2"–Terpyridine as an Energy Absorbing Part," *Proceedings of the 2$^{nd}$ International Conference of f–Elements* 314 (1994).

Mukkala et al., "Influence of Chelating Groups on the Luminescence Properties of Terbium Chelates in 4'–Phenyl–2,2':6',2"–Terpyridine Series," *Proceedings of the 11$^{th}$ International Symposium on the Photochemistry and Photophysics of Coordination Compounds*, 73 (1995).

Latva et al., "Correlation Between the Lowest Triplet State Energy Level of the Ligand and Lanthanide (III) Luminescence Quantum Yield," 75 *Journal of Luminescence* 149–169 (1997).

Takalo et al., "Development of Luminescent Terbium (III) Chelates for Protein Labelling: Effects of Triplet–State Energy Level," 80 *Helvetica Chimica Acta* 372–387 (1997).

Cooper et al., "Syntehsis and Spectral Properties of a New Luminescent Europium (III) Terpyridyl Chelate," 2 *J. Chem. Soc., Perkin Trans.* 1695–1700 (2000).

* cited by examiner

SEQUENCE LISTING
<160> NUMBER OF SEQ ID NOS: 1
<210> SEQ ID NO 1
<211> LENGTH: 12
<212> TYPE: DNA
<213> ORGANISM: Unknown
<220> FEATURE:
<223> OTHER INFORMATION: Model Sequence
<400> SEQUENCE: 1
ttcctccact gt                                                        12

OLIGONUCLEOTIDE LABELING REACTANTS AND THEIR USE

FIELD OF THE INVENTION

This invention relates to novel compounds and methods for labeling of oligonucleotides using machine assisted solid phase chemistry.

BACKGROUND OF THE INVENTION

The publications and other materials used herein to illuminate the background of the invention, and in particular, cases to provide additional details respecting the practice, are incorporated by reference.

Synthetic oligonucleotides tethered to various ligands have been used as research tools in molecular biology [see e.g.: Goodchild, *Bioconjugate Chem.*, 1990, 3, 166; Uhlman and Peyrnan, *Chem. Rev.*, 1990, 90, 543; Sigman, et al. *Chem. Rev.*, 1993, 93, 2295; O'Donnel and McLaughlin in Bioorganic Chemistry, Nucleic Acids, Hecht S M, ed. Oxford Univ. Press, 1996, p. 216]. They have been applied to genetic analysis, and to elucidate mechanism of gene function. Oligonucleotides carrying reporter groups have had widespread use for automated DNA sequencing, hybridization affinity chromatography and fluorescence microscopy. Oligonucleotide-biotin conjugates are widely used as hybridization probes. Antisense oligonucleotides covalently linked to intercalators, chain cleaving or alkylating agents have been shown to be efficient as gene expression regulators. The sequence specific artificial nucleases, when targeted against mRNA, may find applications even as chemotherapeutics.

For several applications, such as in DNA hybridization assays, it is desirable to introduce more than one reporter group to the oligonucleotide structure. This can be performed by three alternative methods:

(i) by coupling several base- or carbohydrate-tethered nucleosidic building blocks to the growing oligonucleotide chain, (ii) by functionalization of the internucleosidic phosphodiester linkages, or (iii) by using several multifunctional non-nucleosidic building blocks during the oligonucleotide chain assembly.

All of these methods have their own drawbacks. Since the double helix formation of DNA is based on hydrogen bonding between the complementary base residues, tethers attached to the base moieties often weaken these interactions. This problem is easily overcome by using the tethered nucleosides at the 3'- or 5'-terminus of the coding sequence, or by using labels linked to C5 of pyrimidine residues. Introduction of tethers to the phosphate backbone gives rise to new chiral centers and makes the purification of these analogues difficult. Introduction of the tether arm to the carbohydrate moiety, in turn, often decreases the coupling efficiency of the phosphoramidite (steric hindrance). Furthermore, synthesis of these blocks is commonly extremely laborious. Although design of non-nucleosidic blocks may look attractive on paper, very often their syntheses suffer from complexity, low coupling yields and problems associated with the storage and handling of the phosphoramidites. For commercial applications design of base tethered nucleosidic building blocks is often the method of choice.

Introduction of linker arms to the nucleobase is most commonly performed by allowing a nucleoside with a good leaving group (N-tosyl, N-benzoyl, halogen, triazole, thiol) at C4 of pyrimidines or C2, C8 or C6 of purines to react with the appropriate nucleophilic linker molecule (e.g. an alkane-α,ω-diamine). Since normally an excess of linker molecule and rather vigorous reaction conditions has to be used, laborious purification procedures cannot be avoided. The basic reaction conditions needed gives additional requirements to the protecting groups in the target molecule. These problems may be overcome by attachment of the linker molecules to C5 of pyrimidine bases by a palladium catalyzed coupling reaction between 5-halogeno pyrimidine 5-mercuriochloro nucleoside and an alkynyl or allyl linker, respectively. However, the method involves rather laborious synthesis of a 5-halogeno or 5-mercuriochloro nucleoside. Very recently, attachment of a linker arm to the N3 of 3',5'-O -protected thymidine based on Mitsunobu reaction [Mitsunobu, Synthesis, 1981, 1] was reported [*J. Org. Chem.*, 1999, 64, 5083; *Nucleosides, Nucleotides*, 1999, 18, 1339]. Since the coupling reaction is performed under mild conditions, a wide range of tether arms can be introduced.

Most of the methods for oligonucleotide tethering described in literature involves attachment of functional groups in the oligonucleotide structure during chain assembly. Hence, introduction of the label molecules has to be performed in solution. In the labeling reaction the additional amino or mercapto groups of oligonucleotides are allowed to react in solution with isothiocyanato, haloacetyl or 2,4,6-triazinyl derivatives of label molecules. Carboxylic acid groups, in turn, can be labeled with amino tethered labels with the aid of water-soluble carbodiimide. Since in all the cases the labeling reaction is performed in aqueous solution with an excess of labeling reactants, laborious purification procedures cannot be avoided. Especially when attachment of several labels is required the isolation and characterization of the desired conjugate is extremely difficult, and often practically impossible. Hence, several attempts to incorporate label molecules or their appropriately protected precursor to oligonucleotide structure during chain assembly have been done [Ruth, J L et al, U.S. Pat. No. 4,948,882; Brush, C K et al, U.S. Pat. No. 5,583,236]. The fluorescent label monomers for solid phase chemistry synthesized are most commonly organic dyes (e.g. fluorescein, rhodamine, dansyl, dabsyl, pyrene, TAMRA) several of these are even commercially available. However, such labels and labeled biomolecules suffer from many commonly known drawbacks such as Raman scattering, other fluorescent impurities, low water solubility, concentration quenching etc. In the specific binding assays, generally very low concentrations of analytes to be measured are present. Thus multilabeling of oligonucleotides with organic fluorophores may not enough enhance detection sensitivity needed in several applications. For these types of applications lanthanide(III) chelates are labels of choice since they do not suffer from this phenomenon. In DNA hybridization assays, time-resolved luminescence spectroscopy using lanthanide chelates is well known [Hemmilä et al. *Bioanalytical Applications of Labelling Technologies*, Wallac Oy, 1994]. Therefore, a number of attempts have been made to develop non-luminescent (DELFIA®) and new highly luminescent chelate labels suitable for time-resolved fluorometric applications. Many patent publications disclose non-luminescent labels [e.g. EP 0064484 A2, EP 0139675 B1, EP 0298939 A1, U.S. Pat. Nos. 4,808,541 and 4,565,790]. Highly luminescent labels include e.g. stabile chelates composed of derivatives of pyridines [U.S. Pat. Nos. 4,920,195, 4,801, 722, 4,761,481, WO 93/11433, U.S. Pat. No. 4,459,186, EP 0770610 A1 and Remuinan et al, *J. Chem. Soc. Perkin Trans*

2, 1993, 1099], bipyridines [U.S. Pat. No. 5,216,134], terpyridines [U.S. Pat. Nos. 4,859,777, 5,202,423 and 5,324,825] or various phenolic compounds [U.S. Pat. Nos. 4,670,572, 4,794,191 and Ital. Pat. 42508 A789] as the energy mediating groups and polycarboxylic acids as chelating parts. In addition, various dicarboxylate derivatives [U.S. Pat. Nos. 5,032,677, 5,055,578 and 4,772,563] macrocyclic cryptates [U.S. Pat. No. 4,927,923, WO 93/5049 and EP 0493745 A1] and macrocyclic Schiff bases [EP 369000 A] have been patented. Also a method for labeling of biospecific binding reactants such as hapten, a peptide, a receptor ligand, a drug or PNA oligomer with luminescent labels by using solid-phase synthesis has been published [EP 067205A1]. One such oligonucleotide labeling reagent has been synthesized and used in multilabeling of oligonucleotides [Kwiatkowski et al. *Nucleic Acids Res.*, 22, 1994, 2604]. However the synthetic strategy described allows only preparation of chelates where the nucleobase is conjugated to the chelate structure limiting the chelate stability and versatility. Furthermore, the structure synthesized is usable only with europium(III) but not with terbium(III), dysprosium(III) or samarium(III).

For some special applications such as helicase assays based on fluorescence energy transfer [Earnshaw et. al, *J. Biomol. Screening*, 4, 1999, 239] large quantities of ultra-pure oligonucleotides bearing a luminescent lanthanide(III) chelate at their 3'- or 5'-terminus are needed. Although these molecules can be obtained by classical labeling methods in solution, yields of the oligonucleotide conjugates can be dramatically improved and purification procedures can be highly simplified if the label could be attached to the oligonucleotide structure during chain assembly. For 5'-derivatization synthesis of nucleosidic or non-nucleosidic building blocks are needed, while 3'-labeling calls for appropriately derivatized polymeric solid supports.

OBJECTS AND SUMMARY OF THE INVENTION

The main objective of the present invention is to improve labeling of oligonucleotides with a desired number of lanthanide(III) chelates.

One objective of the invention is to provide improved labeling reactants for labeling an oligonucleotide.

Another objective of the invention is to provide a highly simplified method for the preparation of nucleosidic building blocks that allow large-scale preparation of oligonucleotide conjugates containing additional functional groups in their structure.

The invention provides improved labeling reactants and a versatile method for direct attachment of a desired number of conjugate groups to the oligonucleotide structure during chain assembly. Hence solution phase labeling and laborious purification procedures can be avoided. The key reaction in the synthetic strategy towards nucleosidic oligonucleotide building blocks is a Mitsunobu alkylation which allows introduction of various labeling reactants to the nucleoside, and finally to the oligonucleotide structure. When oligonucleotides labeled with lanthanide(III) chelates are synthesized, initially precursors of lanthanide(III) chelates are introduced to the oligonucleotide structure during chain assembly, and they are converted to the corresponding lanthanide(III) chelates during deprotection steps.

For some applications, e.g. for helicase assays, ultrapure oligonucleotides bearing a single label molecule at 3'- or 5'-terminus are needed. The present approach for the introduction of lanthanide(III) chelates at these positions on solid phase is also demonstrated.

Thus, the present invention concerns a labeling reactant of formula (I) suitable for labeling an oligonucleotide.

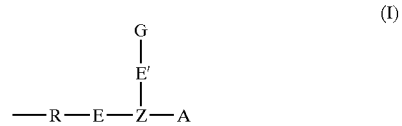

Wherein:

R is a temporary protecting group such as 4,4'dimethoxytrityl (DMTr), 4-methoxytrityl (MMTr), trityl (Tr), (9-phenyl)xanthen-9-yl (pixyl) or not present.

A is either a phosphorylating moiety

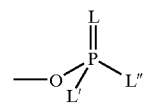

where

L is O, S, or not present

L' is H, L'''CH₂CH₂CN or L'''Ar, where Ar is phenyl or its substituted derivative, where the substituent is nitro or chlorine, and L''' is O or S;

L" is O⁻, S⁻, Cl, N(i-Pr)₂; or

A is a solid support tethered to Z via a linker arm, which is formed of one to ten moieties, each moiety being selected from a group consisting of phenylene, alkylene containing 1–12 carbon atoms, ethynediyl (—C≡C—), ether (—O—), thioether (—S—), amide (—CO—NH—, —NH—CO—, —CO—NR'— and —NR'—CO—), carbonyl (—CO—), ester (—COO— and —OOC—), disulfide (—S—S—), diaza (—N=N—), and tertiary amine (—N—R'), wherein R' represents an alkyl containing less than 5 carbon atoms.

Z is a bridge point and is formed from

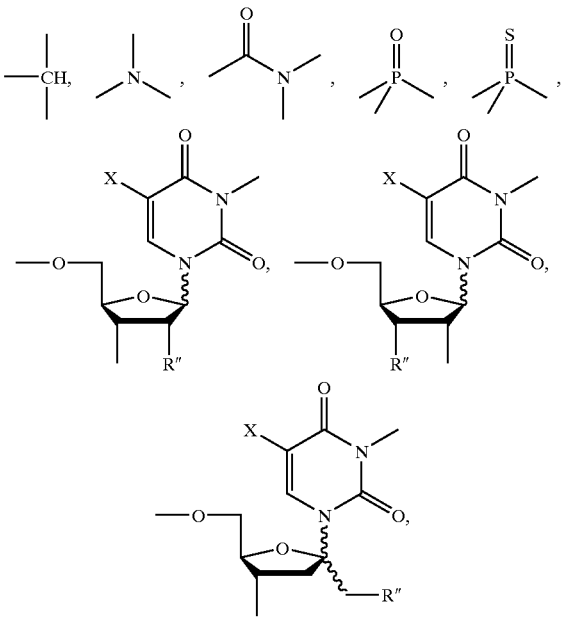

-continued

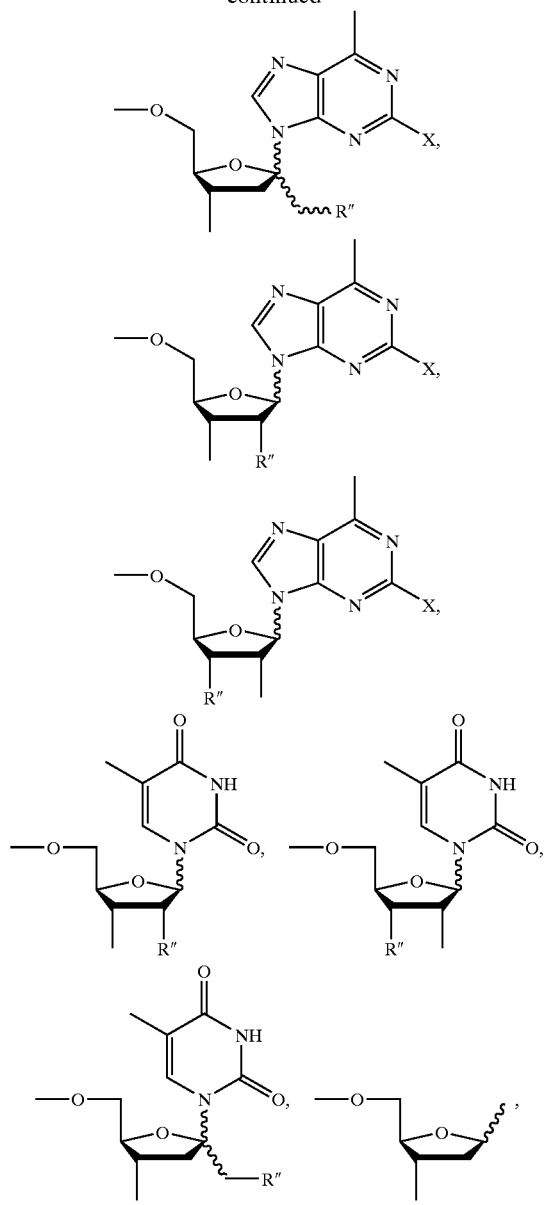

or trivalent derivatives, substituted or unsubstituted, of cyclohexane, cyclohexene, cyclohexadiene, phenyl, cyclopentane, cyclopentene, cyclopentadiene, cyclobutane, cyclobutene, cyclobutadiene, aziridine, diaziridine, oxetane, thietaneazete, azetidine, 1,2-dihydro-1,2-diazete, 1,2-diazetidine, furan, tetrahydrofuran, thiophene, 2,5-dihydrothiophene, thiolane, selenophene, pyrrole, pyrrolidine, phosphole, 1,3-dioxolane, 1,2-dithiole, 1,2-thiolane, 1,3-dithiole, 1,3-dithiolane, oxazole, 4,5-dihydrooxazole, isoxazole, 4,5-dihydoisozaole, 2,3dihydroisoxazole, thiazole, isothiazole, imidazole, imidazolidine, pyrazole, 4,5-dihydropyrazole, pyrazolidine, triazole, pyran, pyran-2-one, 3,4-dihydro-2H-pyran, tetrahydropyran, 4H-pyran, pyran-4-one, pyridine, pyridone, piperidine, phosphabenzene, 1,4-dioxin, 1,4-dithiin, 1,4-oxathiin, oxazine, 1,3-oxazinone, morpholine, 1,3-dioxane, 1,3-dithiane, pyridazine, pyrimidine, pyrazine, piperazine, 1,2,4-triazine, 1,3,5-triazine, 1,3,5-triaza-cyclohexane-2,4,6-trione; where R" is H or X'X", where X' is —O—, —S—, —N—, ON— or —NH— and X" is a permanent protection group such as t-butyldimethylsilyl-, tetrahydropyranyl, 1-(2-fluorophenyl)-4-methoxypiperidin-4-yl-, 1-[2-chloro-4-methyl)phenyl]-4-metoxypiperidin-4-yl-, 4-methoxytetrahydropyran-4-yl-, pthaloyl-, acetyl, pivaloyl-, benzoyl-, 4-methylbenzoyl, benzyl-, trityl or X' is —O— and X" is alkyl or alkoxyalkylalkyl;

X is H, alkyl, alkynyl, allyl, Cl, Br, I, F, S, O, NHCOCH$(CH_3)_2$, NHCOCH$_3$, NHCOPh, SPh$_3$, OCOCH$_3$ or OCOPh.

E is a linker arm between R and Z, and is formed of one to ten moieties, each moiety being selected from a group consisting of phenylene, alkylene containing 1–12 carbon atoms, ethynediyl (—C≡C—), ether (—O—), thioether (—S—), amide (—CO—NH—, —NH—CO—, —CO—NR'— and —NR'—O—), carbonyl (—CO—), ester (—COO— and —OOC—), disulfide (—S—S—), diaza (—N=N—), and tertiary amine (—N—R'), wherein R' represents an alkyl containing less than 5 carbon atoms, or not present.

E' is a linker arm between G and Z, and is formed of one to ten moieties, each moiety being selected from a group consisting of phenylene, alkylene containing 1–12 carbon atoms, ethynediyl (—C≡C—), ether (—O—), thioether (—S—), amide (—CO—NH—, —NH—CO—, —CO—NR'— and —NR'—CO—), carbonyl (—CO—), ester (—COO— and —OOC—), disulfide (—S—S—), diaza (—N=N—), and tertiary amine (—N—R'), wherein R' represents an alkyl containing less than 5 carbon atoms, or not present.

G is a bivalent aromatic structure, tethered to two iminodiacetic acid ester groups N(COOR''')$_2$, where R''' is an alkyl of 1 to 4 carbon atoms, allyl, ethyltrimethylsilyl, phenyl or benzyl, which phenyl or benzyl can be substituted or unsubstituted, and said bivalent aromatic structure is capable of absorbing light or energy and transferring the excitation energy to a lanthanide ion after the solid phase synthesis made labeling reactant has been released from the used solid support, deprotected and converted to a lanthanide chelate, or G is a structure selected from a group consisting of

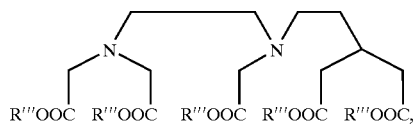

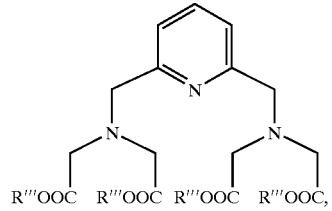

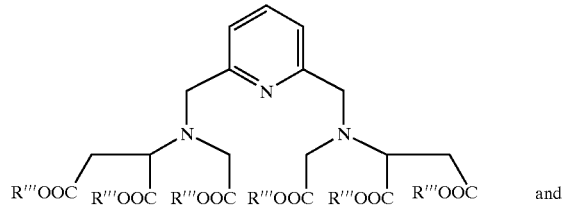

and

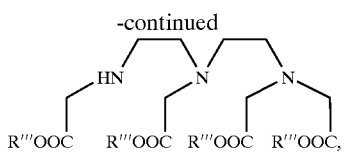

where
R''' is an alkyl of 1 to 4 carbon atoms, allyl, ethyltrimethylsilyl, phenyl or benzyl, which phenyl or benzyl can be substituted or unsubstituted, and one of the hydrogen atoms is substituted with E', or G is a protected functional group, where the functional group is amino, aminooxy, carboxyl, thiol, and the protecting group is pthaloyl, trityl, 2-(4-nitrophenyl-sulfonyl) ethoxycarbonyl, fluorenylmethyloxycarbonyl, benzyloxycarbonyl or t-butoxycarbonyl for amino and aminooxy, alkyl for carbonyl and alkyl or trityl for thiol provided that bridge point Z is selected from a group consisting of

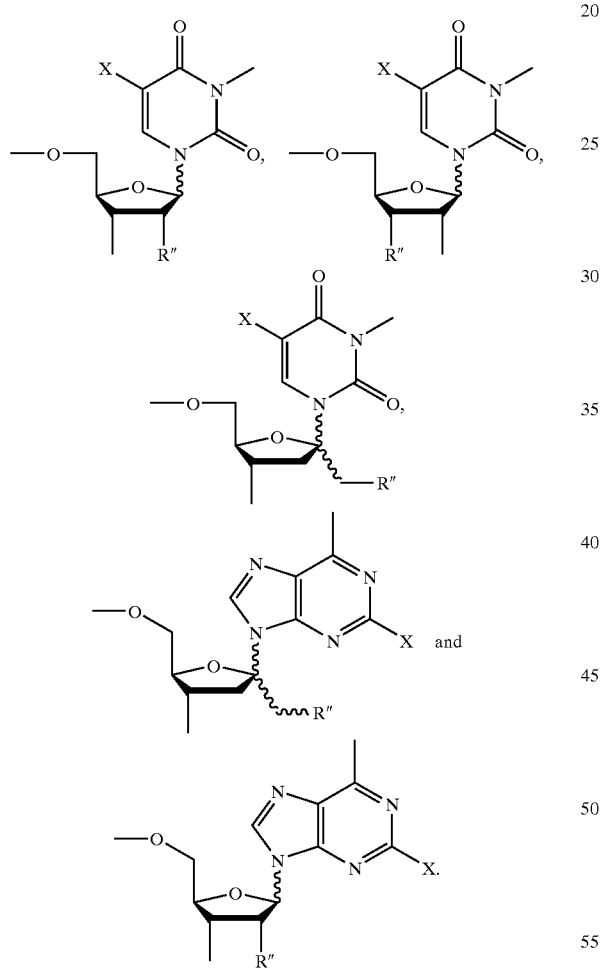

The present invention further concerns a method for direct attachment of a conjugate group to an oligonucleotide structure enabling the attachment of a desired number of these groups during chain assembly. Said method comprises a Mitsunobu alkylation of a compound of formula (II).

R—Z'         (II)

Wherein:
R is a temporary protecting group such as DMTr, MTfr, Tr, or pixyl.

Z' is an acidic bridge point selected from a group consisting of

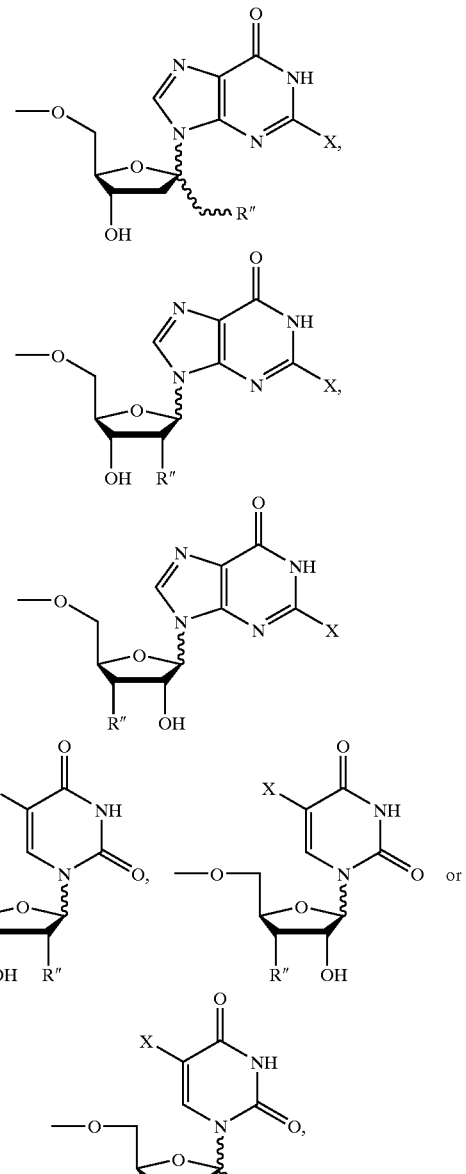

where
R'' is H or X'X'', where X' is —O—, —S—, —N—, ON— or —NH— and X'' is a permanent protection group such as t-butyldimethylsilyl-, tetrahydropyranyl, 1-(2-fluorophenyl)-4-methoxypiperidin-4-yl-, 1-[2-chloro-4-methyl)phenyl]-4-metoxypiperidin-4-yl-, 4-methoxytetrahydropyran-4-yl-, pthaloyl-, acetyl, pivaloyl-, benzoyl-, 4-methylbenzoyl-, benzyl-, trityl or alkyl;

X is H, alkyl, alkynyl, allyl, Cl, Br, I, F, S, O, NHCOCH$(CH_3)_2$, NHCOCH$_3$, NHCOPh, SPh$_3$, OCOCH$_3$ or OCOPh;

and pK$_a$ of said acidic bridge point is <14.

Said compound of formula (II) is alkylated with a compound of formula(III).

G—E″ (III)

Wherein:

E″ is an arm with a primary aliphatic OH group at the end, which arm is formed of one to ten moieties, each moiety being selected from a group consisting of phenylene, alkylene containing 1–12 carbon atoms, ethynediyl (—C≡C—), ether (—O—), thioether (—S—), amide (—CO—NH—, —NH—CO—, —CO—NR'— and —NR'—CO—), carbonyl (—CO—), ester (—COO— and —OOC—), disulfide (—S—S—), diaza (—N=N—), and tertiary amine (—N—R'), wherein R' represents an alkyl containing less than 5 carbon atoms.

G is a bivalent aromatic structure, tethered to two iminodiacetic acid ester groups N(COOR''')$_2$, where R''' is an alkyl of 1 to 4 carbon atoms, allyl, ethyltrimethylsilyl, phenyl or benzyl, which phenyl or benzyl can be substituted or unsubstituted and said bivalent aromatic structure is capable of absorbing light or energy and transferring the excitation energy to a lanthanide ion after the solid phase synthesis made labeling reactant has been released from the used solid support, deprotected and converted to a lanthanide chelate, or G is a structure selected from a group consisting of

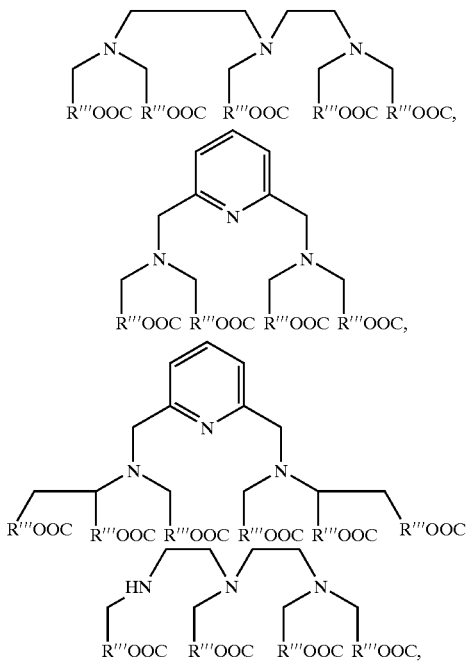

where

R''' is an alkyl of 1 to 4 carbon atoms, allyl, ethyltrimethylsilyl, phenyl or benzyl, which phenyl or benzyl can be substituted or unsubstituted, and one of the hydrogen atoms is substituted with E', or G is a protected functional group, where the functional group is amino, aminooxy, carboxyl, thiol, and the protecting group is pthaloyl, trityl, 2-(4-nitrophenyl-sulfonyl)ethoxycarbonyl, fluorenylmethyloxycarbonyl, benzyloxycarbonyl or t-butoxycarbonyl for amino and aminooxy, alkyl for carbonyl and alkyl or trityl for thiol, or G is not present.

The functional groups of E' and G, excluding said primary aliphatic OH group, are protected.

A compound of formula (IV)

is provided.

Wherein: G and R of compound (IV) are as defined above;

E''' is a linker arm between G and Z, and is formed of one to ten moieties, each moiety being selected from a group consisting of phenylene, alkylene containing 1–12 carbon atoms, ethynediyl (—C≡C—), ether (—O—), thioether (—S—), amide (—CO—NH—, —NH—CO—, —CO—NR'— and —NR'—CO—), carbonyl (—CO—), ester (—COO— and —OOC—), disulfide (—S—S—), diaza (—N=N—), and tertiary amine (—N—R', wherein R' represents an alkyl containing less than 5 carbon atoms; and Z″ is a bridge point selected from a group consisting of

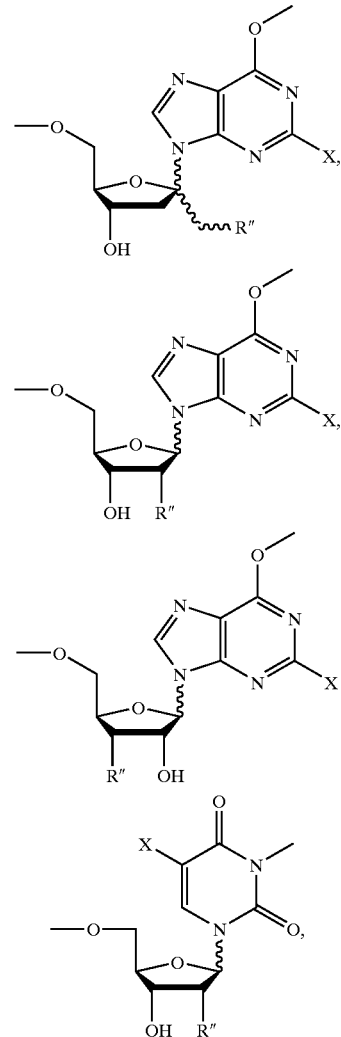

-continued

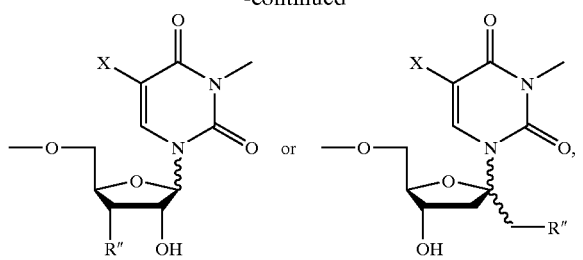

where
R''' is H or X'X'', where X' is —O—, —S—, —N—, ON— or —NH— and X'' is a permanent protection group such as t-butyldimethylsilyl-, tetrahydropyranyl, 1-(2-fluorophenyl)-4-methoxypiperidin-4-yl-, 1-[2-chloro-4-methyl)phenyl]-4-metoxypiperidin-4-yl-, 4-methoxytetrahydropyran-4-yl-, pthaloyl-, acetyl, pivaloyl-, benzoyl-, 4-methylbenzoyl, benzyl-, trityl or alkyl;

X is H, alkyl, alkynyl, allyl, Cl, Br, I, F, S, O, NHCOCH$(CH_3)_2$, NHCOCH$_3$, NHCOPh, SPh$_3$, OCOCH$_3$ or OCOPh.

ADVANTAGES AND KEY STEPS OF METHOD FOR OLIGONUCLEOTIDE DERIVATIZATION

The present invention for oligonucleotide derivatization combines several important features:

(i) The nucleosidic protected functional group tethered building blocks can be synthesized in a few days using cheap reagents, equimolar reagent ratios, and simple purification procedures. The starting materials are commercially available and can also be prepared in a single step using standard well-documented textbook protocols [Gait, M. Oligonucleotide Synthesis, a Practical Approach, IRL Press, 1990]. The key reaction in the present invention is the Mitsunobu alkylation of the above mentioned 5'-O-protected nucleoside and the appropriate linker molecule i.e. a primary alcohol where additional functional groups are protected. Under the reaction conditions employed 3'-O-protection of the nucleoside is not required. These nucleosides are finally converted to the corresponding phosphoramidites in conventional manner, and they can be purified either by precipitation from cold hexanes, or by silica gel column chromatography. Since the products are solids, their storage and handling does not suffer from the problems associated with oily non-nucleosidic phosphoramidites.

(ii) Since the coupling reaction between the nucleoside and the tether molecule is performed under mild reaction conditions [at ambient temperature in dry tetrahydrofuran (THF)] using equimolar reagent ratios, a wide range of tethers can be introduced. The only requirement is that the tether molecule has a primary hydroxyl group in its structure, and other functional groups are protected. Hence very complicated molecules can be incorporated to the nucleoside (and finally to the oligonucleotide structure) in high efficiency. These tethers with conjugate groups for different applications can be:

(a) fluorescent or chemiluminescent groups or spin-labels,
(b) chemically reactive groups that induce irreversible reactions to their target sequences, or
(c) groups that promote intermolecular interactions (e.g. biotin).

Representative structures synthesized according to the method of the present invention are presented in schemes 2–11.

(iii) Since the building blocks are derivatives of nucleosides bearing tether arm attached to the base moiety, they can be coupled to the oligonucleotide chain using standard protocols in high efficiency (i.e. no changes in concentrations or coupling times required).

(iv) Since the tether arm is attached to the base moiety, multilabeling of oligonucleotides is achievable.

(v) If a ligand structure/structures is/are incorporated to the oligonucleotide chain during chain assembly, it/they can be converted to the corresponding lanthanide(III) chelates during slightly modified deprotection steps. Hence laborious solution phase labeling as well as synthesis of the activated chelates and oligonucleotides tethered to functional groups can be avoided.

(vi) For several applications introduction of only a single label molecule at the 5'-terminus of the oligonucleotide structure is needed. For these applications the ligand structures can be simplified by omitting the nucleobase from the structure i.e. resulting in non-nucleosidic phosphoramidite building blocks. Examples of such a molecules are shown in examples 22 and 33.

(vii) For the preparation of 3'-tethered oligonucleotides the ligand structures can be converted also to the corresponding non-nucleosidic or nucleosidic solid supports that can be used in solid phase oligonucleotide synthesis. The solid support can be either a long chain alkylamine controlled pore glass (LCAA) or polystyrene. An example of such a solid support is shown in example 24.

(viii) Several of the structures described above can be obtained also by using slightly modified reaction routes:

(a) A nucleoside tethered to an alkynyl group is synthesized by Mitsunobu alkylation, the ligand structure is coupled to it as an aromatic halide using Sonagoshira reaction.
(b) A nucleoside tethered to a protected functional group is synthesized using Mitsunobu reaction, the protecting group is selectively removed (e.g. ammonolysis for trifluoroacetylamido), and the ligand or label structure is coupled by carbodiimide assisted reaction.

DETAILED DESCRIPTION OF THE INVENTION

The novel labeling reactants and labeling methods of the present invention are particularly suitable for the preparation of oligonucleotide conjugates bearing a desired known number of functional groups or label molecules in their structure.

The term 'bivalent' in the definition of G shall mean a chemical group bound to two neighboring atoms.

The functional groups most suitable are amino, carboxyl, aminooxy or thiol.

The most suitable chelates are non-luminescent and luminescent lanthanide(III) chelates.

The organic dyes suitable for monolabeling are dabsyl, dansyl, fluorescein, rhodamine or TAMRA.

A particularly preferable transient protecting group R is 4,4'-dimethoxytrityl

The sugar of the nucleotide is preferably ribose or 2-deoxyribose. In the former case the permanent protecting group X" for hydroxyl is preferably t-butyldimethylsilyl, tetrahydropyranyl, 1-(2-fluorophenyl)-4-methoxypiperidin-4-yl-(Fpmp), 1-[2-chloro-4-methyl)phenyl]-4-methoxypiperidin-4-yl- or 4-methoxytetrahydropyran4-yl-, or X" is an alkyl or alkoxalkyl, preferably methyl, methoxymethyl or etoxymethyl.

For luminescent labeling reactants G is a bivalent aromatic structure and is preferably selected from a group consisting of carbostyryl or structures disclosed in Scheme 1A. For non-luminescent labeling reactants G is selected from a group of structures disclosed in 1B.

The substituent R'" is preferably methyl, ethyl or allyl.

Most preferably, the labeling reactant is 2'-deoxy-5'-O-(4,4'-dimethoxytrityl)-N3 {tetramethyl 2,2',2",2'"-[(4(1-hexyn-5-yl)pyridine-2,6-diyl)bis(methylennenitrilo)}tetrakis(acetato) uridine 3'-O-(2-cyanoethyl N,N-diisopropyl)phosphoramidite (7), N3-[6-[4-(dimethylamino)azobenzene-4'-sulfonamido]hex-1-yl-5'-O-(4,4'-dimethoxytrityl)thymidine 3'-O-(2-cyanoethyl N,N-diisopropyl) phosphoramidite (12), 5'-O-(4,4'-dimethoxytrityl)-N3-{tetramethyl-2,2',2",2'"-{6,6'-[4'-hydroxyethoxyethoxyphenylethynyl]pyridine-2,6-diyl}bis(methylenenitrilo)tetrakis(acetato)}thymidine 3'-O-(2-cyanoethyl N,N-diisopropyl) phosphoramidite (18), 2'-deoxy-5'-O-(4,4'-dimethoxytrityl) tetramethyl-2,2',2",2'"-{{6,6'-[4-(6-hydroxyhexyl)-1H-pyrazol-1,3-diyl]bis-(pyridine)-2,2'-diyl}bis(methylenenitrilo)}tetrakis(acetato)-6-O-(2-cyanoethyl) N,N-diisopropyl)phosphoramidite (25), 2'-deoxy-5'-O-(4,4'-dimethoxytrityl)-3-6-{{4-{6,6"-bis[N,N-bis(methoxycarbonylmethyl)aminomethyl]-2,2':6',2"-terpyridine-4'-yl}phenyl}hex-5-yn-1-yl}-uridine 3'-[O-(2-cyanoethyl)-N,N-diisopropyl]phosphoramidite (37) or 6-{4-{6,6"-bis[N,N-bis(methoxycarbonylmethyl) aminomethyl]-2,2':6',2"-terpyridine-4'-yl}phenyl}hex-5-yn-1-ol [O-(2-cyanoethyl)-N,N diisopropyl]-phosphoramidite (38).

Most preferably the solid support is 5'-O-(4,4'-dimethoxytrityl)-3'-O-succinyl-N3-{tetramethyl-2,2',2",2'"-{6,6'-[4'-hydroxyethoxyethoxyphenylethynyl]pyridine-2,6-diyl}bis(methylenenitrilo)tetrakis(acetato))thymidine long chain alkylamine controlled pore glass (24).

According to a preferred embodiment the lanthanide chelate is a europium(III), terbium(III), samarium(III) or dysprosium(III) chelate.

The invention is further elucidated by the following examples. The structures and synthetic routes employed in the experimental part are depicted in schemes 2–9. Scheme 2 illustrates the synthesis of the labeling reagents 3 and 4. The experimental details are given in examples 14. Schemes 3A and 3B illustrate the synthesis of the labeling reagent 8. Scheme 4 illustrates synthesis of the labeling reagent 12. The experimental details are given in examples 10–12. Schemes 5A and 5B illustrate the preparation of the labeling reagent 18. Experimental details are given in examples 13–16. Scheme 6A and 6B illustrate the synthesis of labeling reagent 25. Experimental details are given in examples 18–22. Scheme 7A and 7B illustrate the synthesis of the solid support 27. Experimental details are presented in examples 23 and 24. Scheme 8A and 8B illustrate the synthesis of labeling reagents 37 and 38. Experimental details are given in examples 25–33. Scheme 9 illustrates the introduction of primary amino groups to the oligonucleotide structure in the aid of compound 8 as well as further oligonucleotide derivatization in solution. Experimental details are given in example 35. Scheme 10 illustrates introduction of lanthanide(III) chelates to the oligoncletide structure in with the aid of compound 8. Experimental details arc given in example 36. Scheme 11 illustrates introduction of lanthanide(III) chelates to the oligonucleotide structure in with the aid of compound 38. Experimental details are given in example 37.

EXPERIMENTAL PROCEDURES

Reagents for machine assisted oligonucleotide synthesis were purchased from PE Biosystems (Foster City, Calif.). 2-Cyanoethyl-N,N,N',N'-tetraisopropylphosphodiamidite, N6-trifluoroacetamidohexanol and 2'-deoxy-5'-O-(4,4'-dimethoxytrityl)-uridine and 5'-O-(4,4'-dimethoxy-trityl) thymidine were synthesized according to published procedures. Adsorption column chromatography was performed on columns packed with silica gel 60 (Merck). NMR spectra were recorded on a Jeol LA-400 spectrometer operating at 399.8, 350, 161.9 and 100.5 MHz for $^1$H, $^{19}$F $^{31}$P and $^{13}$C, respectively, or on a Jeol GX 500 instrument operating at 500.00 and 125.65 MHz for $^1$H and $^{13}$C, respectively. Me$_4$Si was used as an internal ($^1$H and $^{13}$C) and H$_3$PO$_4$ ($^{31}$P) and trifluoroacetic acid ($^{19}$F) as external references. Coupling constants are given in Hz. When reported, signal characterization is based on $^1$H,$^1$H, $^1$H, $^{13}$C and $^{13}$C,$^{13}$C COSY experiments. IR spectra were recorded on a Perkin Elmer 2000 FT-IR spectrophotometer. Fast atom bombardment mass spectra were recorded on a VG ZabSpec-ao TOF instrument in the positive detection mode. Oligonucleotides were assembled on an Applied Biosystems 932 DNA Synthesizer using phosphoramidite chemistry and recommended protocols (DMTr-Off-synthesis).

EXAMPLE 1

The Synthesis of 2'-deoxy-5'-O-(4,4'-dimethoxytrityl)-N3-(N6-trifluoroacetamidohex-1-yl)uridine (1)

2'-Deoxy-5'-O-(4,4'-dimethoxytrityl)uridine (8.0 g, 15.1 mmol), Ph$_3$P (4.7 g, 17.9 mmol) and N6-trifluoroacetamidohexan-1-ol (4.1 g, 18.1 mmol) were dissolved in dry THF (80 ml). DEAD (2.85 ml) was added in five portions during 15 min, after which the mixture was stirred 2 h at ambient temperature and concentrated. Purification on silica gel (eluent diethyl ether) yielded 65% of 2.
$^1$H NMR (DMSO-d$_6$; 500 MHz): δ 9.41 (1H, br, NH); 7.72 (1H, d, H-6); 7.35 (2H, DMTr); 7.25 (7H, DMTr); 6.85 (4H, d, DMTr); 5.5 (1H, d, H-5), 6.2 (1H, t, H-1'), 5.4 (1H, d, 3'-OH), 4.3 (1H, m, H-4'), 4.3 (1H, m, H-3'), 3.9 (1H, m, H-4'), 3.5 (1H, dd, H-5'), 3.8 (2H, t), 3.2 (1H, H-5'), 3.15 (2H, m), 2.2 (2H, H-2'; H-2"), 1.5 (4H, m); 1.25 (4H, m). $^{13}$C NMR (DMSO-d$_6$): δ 161.7 (C4), 158.0 (C=O), 156.5 (q, CF$_3$); 150.3 (C2); 144.8 (DMT); 138.8 (C6); 129.7, 127.8, 127.7, 126.7, 113.1 (DMT); 100.7 (C-5), 85.7 (DMT); 85.5 (C4'); 85.2 (C1'); 69.8 (C3'); 63.3 (C5'); 55.5 (2.OMe); 40.1 (NCH$_2$); 39.7 (C2'); 39.0 (CH$_2$NHCO); 28.0, 25.9, 25.8 (CH$_2$) $^{15}$N NMR (DMSO-d$_6$): δ−294.5 (NHCOCF$_3$); −264.0 (N1); −244.6 (N3).

EXAMPLE 2

The Synthesis of 5'-O-(4,4'-dimethoxytrityl)-N3-(N6-tifluoroacetamidohexyl)thymidine (2)

The title compound was synthesized as described in example 1 for compound 1 by using 5'-O-(4,4'-dimethoxytrityl)thymidine as the starting material. The yield was 76%. $^1$H NMR (DMSO-d$_6$; 500 MHz): δ 9.35 (1H, br t, J 5.2, NH); 7.54 (1H, d, J 1.1, H-6); 7.38–7.23 (9H, DMT); 6.88 (4H, d, DMT); 6.22 (1H, t, J 6.6, H-1'); 5.31 (1H, d, J 4.6, 3'-OH); 4.31 (1H, m, H-3'); 3.89 (1H, m, H4'); 3.77 (2H, m, NCH$_2$); 3.72 (6H, s, 2.OCH$_3$); 3.21 (1H, dd, J 5.8 and 10.6 H-5'); 3.16 (1H, dd, J 3.0 and 10.6, H-5'); 3.15 (2H, m, CH$_2$NH); 2.24 (1H, m, H-2"); 2.17 81H, m, H-2'); 1.49 (3H, d, J 1.1 5-CH$_3$); 1.48 (2H, m, NCH$_2$CH$_2$); 1.45 (2H, m, CH$_2$ CH$_2$NH); 1.26 (4H, m, 2 . CH$_2$). $^{13}$C NMR (DMSO-d$_6$) δ: 162.5 (C4), 158.1 (C=O), 156.1 (q, J$_{C,F}$ 35.9, CF$_3$); 150.2 (C2); 144.7 (DMT); 134.3 (C6); 129.7, 127.8, 127.66, 126.7, 113.1 (DMT); 108.7 (C-5), 85.7 (DMT); 85.6 (C4'); 84.8 (C1'); 70.4 (C3'); 63.7 (C5'); 55.0 (2.OMe); 40.4 (NCH$_2$); 39.7 (C2'); 39.0 (CH$_2$NH—CO); 28.0, 26.9, 25.9, 25.8 (CH$_2$).

EXAMPLE 3
The Synthesis of 2'-deoxy-5'-O-(4,4'-dimethoxytrityl)-N3-(N6-trifluoroacetamidohexyl)uridine 3'-O-(2-cyanoetlyl N,N-diisopropyl)phosphoramidite (3)
Predried compound 1 and 2-cyanoethyl N,N,N',N'-tetraisopropylphosphordiamidite (1.5 eq) were dissolved in dry acetonitrile. 1H tetrazole (1 eq; 0.45 M in acetonitrile) was added, and the mixture was stirred for 30 min at room temperature before being poured into 5% NaHCO$_3$ and extracted with dichloromethane and dried over Na$_2$SO$_4$. Precipitation from cold (−70° C.) hexane yielded the title compound as a white powder. Compound 3: $^{31}$P NMR (CDCl$_3$): δ 148.6 (0.5 P), 148.4 (0.5 P).

EXAMPLE 4
The Synthesis of 5'-O-(4,4'-dimethoxytrityl)-N3-(N6trifluoroacetamidohexyl)thymidine 3'-O-(2-cyanoethyl N,N-diisopropyl)phosphoramidite (4)
Phosphitylation of compound 2 as described in example 3 for compound 1 yielded the title compound as a white powder. Compound 4: $^{31}$P NMR (CDCl$_3$): δ 148.6 (0.5 P), 148.4 (0.5 P).

EXAMPLE 5
The Synthesis of tetramethyl 2,2',2'', 2'''-[4-(6-hydroxyhex-5-yn-1-yl)pyridine-2,6-diyl)bis(methylenenitrilo)]tetrakis (acetate) (6)
A mixture of tetramethyl 2,2',2'',2'''-[4bromopyridine-2,6-diyl)bis(methylenenitrilo)tetrakis(acetate) (5), bis (triphenylphosphinepalladium(II) chloride and CuI in dry THF and triethylamine was deaerated with argon. 5-hexynol was added and the mixture was stirred for 7 h at 55° C. The cooled solution was filtered; the filtrate was evaporated and redissolved in dichloromethane. The solution was washed with water, dried and concentrated. Purification on silica gel yielded the title compound as an oil (75 %). Compound 6: $^1$H NMR (CDCl$_3$; 400 MHz): 7.46 (2H, s); 3.99 (4H, s); 3.71 (12H, s, 4 CH$_3$); 3.62 (8H, s, 4 CH$_2$); 2.53 (4H, m, CH$_2$); 1.70 (4H, m, 2 CH$_2$) IR (neat): 2242 (C≡C).

EXAMPLE 6
The Synthesis of 2'-deoxy-5'-O-(4,4'-dimethoxytrityl)-N3 {tetramethyl 2,2',2'', 2'''-[(4-(hex-5-yn-1-yl)pyridine-2,6-diyl)bis(methylenenitrilo)}tetrakis(acetato)uridine (7)—Method A
2'-Deoxy-5'-O-(4,4'-dimethoxytrityl)uridine was allowed to react with compound 6 as described in example 1. Purification on silica gel (eluent CH$_2$Cl$_2$: MeOH 95:5, v/v) yielded the title compound as foam. The yield was 70%. Compound 7:
$^1$H NMR (DMSO-d$_6$; 500 MHz): δ 7.67 (1H, d, J 8.2, H-6); 7.36 (2H, s, pyridine); 7.35 (2H, DMTr); 7.25 (7H, DMTr); 6.85 (4H, d, DMTr); 6.16 (1H, t, H-1, J 6.3); 5.48 (1H, d, J 8.1, H-5); 5.34 (1H, d, J 4.8, 3'-OH); 4.29 (1H, m, H-3'); 3.89 (1H, m, H-4'); 3.86 (4H, s, 2.CH$_2$); 3.82 (2H, t, J 5.6 Ar—CH$_2$); 3.58 (8H, s, 4.CH$_2$), 3.24 (1H, dd, J 10.7 and 5.2, H-5'); 3.19 (1H, dd, J 3.1 and 10.7, H-5"); 2.50 (2H, t, CH$_2$); 2.20 (2H, t, H-2' and H-2"); 2.72 (1H, br, OH) 1.73 (2H, m, CH$_2$); 1.52 (2H, m, CH$_2$).

EXAMPLE 7
Synthesis of 2'-deoxy-5'-O-(4,4'-dimethoxytrityl)-N3 (hex-5-yn-1-yl)uridine (9)
5-Hexynol was allowed to react with 2'-deoxy-5'-O-(4,4'-dimethoxytrityl)uridine under Mitsunobu conditions described in example 1. Purification on silica gel (eluent diethyl ether) yielded the title compound as a solid (86%) Compound 9:
$^1$H NMR (DMSO-d$_6$, 400 MHz): δ 7.70 (1H, d, J 8.1, H-6); 7.39 (2H, DMT); 7.31 (2H, DMT); 7.25 (5H, DMT); 6.90 (4H, d, J 8.0); 6.18 (1H, t, J 6.3, H-1'); 5.49 (1H, J 8.1, H-5); 5.38 (1H, d, J 4.6, 3'-OH); 4.31 (1H, m, H-3'); 3.90 (1H, m, H-4'); 3.78 (2H, m, NCH$_2$); 3.74 (6H, s, 2.OCH$_3$); 3.26 (1H, dd, J 5.4 and 10.7, H-5'); 3.19 (1H, dd, J 2.9 and 10.7, H-5"); 2.23 (3H, H-2', H-2" and CH$_2$C≡); 1.63 (2H, p, CH$_2$); 1.47 (1H, t, ≡CH); 1.43 (2H, p, CH$_2$).

EXAMPLE 8
The Synthesis of 2'-deoxy-5'-O-(4,4'-dimethoxytrityl)-N3 {tetramethyl 2,2',2'', 2'''-[(4-(hex-5-yn-1-yl)pyridine-2, 6diyl)bis(methylene-nitrilo)}tetrakis(acetato)uridine (7)
Method B
Compound 9 was coupled to compound 5 using the method described in example 5. The yield was 60%. The product was spectroscopically and chromatographically identical with the material synthesized in example 6.

EXAMPLE 9
The Synthesis of 2'-deoxy-5'-O-(4,4'-dimethoxytrityl)-3-{6-{2,6-bis[N,N-bis(methoxycarbonylmethyl)aminomethyl] pyridin-4-yl}hex-5-yn-1-yl}uridine 3'-[O-(2-cyanoethyl)-N, N-diisopropyl]phosphoramidite (8)
Compound 7 was phosphitylated using the method described in example 2. Purification was performed on silica gel (eluent CH$_2$Cl$_2$:Et$_3$N:MeOH 90:10:5; v/v/v). Compound 8: $^{31}$P NMR (CDCl$_3$): δ 149.4 (0.5 P), 149.1 (0.5 P).

EXAMPLE 10
The Synthesis of 6-[4-(dimethylamino)azobenzene-4'-sulfonamido]hexan-1-ol (10)
To a stirred solution of 6-aminohexan-1-ol (0.50 g, 4.27 mmol) in dichloromethane (10 ml) was added dropwise a solution of dabsyl chloride (0.5 g, 1.54 mmol) in dichloromethane (10 ml). After 1 h the mixture was washed with sat aq. NaHCO$_3$. The organic layer was dried over Na$_2$SO$_4$ and concentrated. Purification on silica gel (eluent CH$_2$Cl$_2$ containing 1% (v/v) MeOH) yielded the title compound as red solid. Compound 10: $^1$H NMR (CDCl$_3$): δ 7.97–7.89 (6H, m); 6.76 (2H, d, J 9.3); 4.50 (1H, br t, J 6.3); 3.60 (2H, t, J 6.2); 3.13 (6H, s); 2.98 (2H, q, J 6.9); 1.63 (1H, br); 1.50 (4H, m); 1.30 (4H, m).

EXAMPLE 11
The Synthesis of N3-[6-[4-(dimethylamino)azobenzene-4'-sulfonamido]hex-1-yl-5'-O-(4,4'-dimethoxytrityl)thymidine (11)
The title compound was synthesized by Mitsunobu alkylation of 5'-O-(4,4'-dimethoxytrityl)thymidine and compound 10 using procedures described in example 1. The yield was 74%. Compound 11: $^1$H NMR (400 MHz, DMSO-d$_6$): d 7.98–7.88 (6H, m, dabsyl); 7.57 (1H, J 1.2 H-6); 7.40 (2H, d, DMT); 7.30–7.24 (7H, m, DMT); 6.83 (4H, d, J, 9.0, DMT), 6.75 (2H, d, J 7.3, dabsyl); 6.48 (1H, dd, J 7.8), 5.03 (1H, t, J6.1, NH); 4.55 (1H, m, H-3'); 4.07 (1H, m, H-4'); 3.92 (2H, m, NCH$_2$); 3.79 (6H, s, 2.OCH$_3$); 3.46 (1H, dd, J 3.2 and 10.5, H-5'); 3.36 (1H, dd, J 2.9 and 10.5, H-5"); 3.12 (6H, s, N(CH$_3$)$_2$); 2.99 (2H, m, CH$_2$NH); 2.46 (1H, m, H-2"); 2.31 (1H, m, H-2' and 3'-OH); 1.59 (4H, m, 2.CH$_2$); 1.38–1.25 (4H, m, 2.CH$_2$).

EXAMPLE 12
The Synthesis of N3-[6-[4-(dimethylamino)azobenzene-4'-sulfonamido]hex-1-yl-5'-O-(4,4'-dimethoxytrityl)thymidine 3'-O-(2-cyanoethyl N,N-diisopropyl) phosphoramidite (12)

Phosphitylation of compound 11 as described in example 3 yielded the title compound as a solid (purification on silica gel using the eluent described in example 9).

EXAMPLE 13
The Synthesis of Tritylethoxyethanol (13)

Bisethoxyethanol (10 ml) was dried by coevaporation with dry pyridine and dissolved in the same solvent (20 ml). Trityl chloride was added and the mixture was stirred 2 h at ambient temperature. The solvent was evaporated in vacuo. The residue was dissolved in methylene chloride, washed with sat. NaHCO$_3$, dried (Na$_2$SO$_4$) and concentrated. Precipitation from ethyl ether yielded the title compound as a white powder. It was used in the next step without further characterization.

EXAMPLE 14
The Synthesis of 4-iodophenoxyethoxyethanol (14)

Compound 13 was allowed to react with 4-iodophenol as described in example 1. When the reaction was completed (ca. 2 h) the solvent was evaporated off and the residue was suspended in diethyl ether and passed though a short column of silica gel. The eluent was removed in vacuo and the residue was dissolved in the mixture of TFA and ethanol (9:1, v/v) and stirred overnight at ambient temperature after being concentrated. The residue was taken in methylene chloride and washed with sat. NaHCO$_3$, dried (Na$_2$SO$_4$) and concentrated. Purification was performed on silica gel. The column was eluted initially with methylene chloride to remove trityl carbinol and then with the mixture of CH$_2$Cl$_2$:MeOH (9:1, v/v) to elute the desired product. Compound 14: $^1$H NMR (CDCl$_3$): δ 7.53 (2H, d, J 9.0); 6.68 (2H, d, J 9.0); 4.07 (2H, m); 3.83 (2H, m); 3.73 (2H, m); 3.64 (2H, m); 2.26 (1H, br).

EXAMPLE 15
The synthesis of tetramethyl 2,2',2",2"'-}6,6'-[4'-hydroxyethoxyethoxyphenoxyethynyl]pyridine-2,6-diyl bis (methylene-nitrilo)tetrakis(acetate) (16)

Compound 14 was allowed to react with tetramethyl 2,2',2",2"'-[4-ethynylpyridine-2,6-diyl)bis(methylenenitrilo) tetrakisacetate 15 using the reaction described in example 5, but reaction was completed in 5 h at ambient temperature. Compound 15:: $^1$H NMR (CDCl$_3$): δ 7.53 (2H, s); 7.49 (2H, d, J 8.8); 6.98 (2H, d, J 8.8); 4.17 (2H, m); 4.03 (4H, s); 3.89 (2H, m); 3.79 (2H, m); 3.72 (12H, s); 3.68 (2H, m); 3.64 (8H, s); 2.38 (1H, br).

EXAMPLE 16
The synthesis of 5'-O-(4,4'-dimethoxytrityl)-N3-{tetramethyl-2,2',2",2"'-{6,6'-[4'-ethoxyethoxyphenoxyethynyl]pyridine-2,6-diyl}bis (methylenenitrilo)tetrakis(acetato)}thymidine (17)

Compound 16 was allowed to react with 5'-O-(4,4'-dimethoxytrityl)thymidine using the reaction described in example 1. Compound 17: $^1$H NMR (DMSO-$_6$): d 7.59 (1H, s); 7.51 (2H, d, J 8.8); 7.47 (2H, s); 7.49–7.23 (9H, DMT); 6.99 (2H, d, J 8.8); 6.86 (4H,d, DMT); 6.23 (1H, t, J 6.8); 5.34 (1H, d, J 4.2; exch. with D$_2$O); 4.32 (1H, m); 4.10 (2H, m); 4.01 (2H, m); 3.92 (1H, m); 3.90 (4H, s); 3.74 (2H, m); 3.71 (12H, s); 3.62 (2H, m); 3.61 (8H, s); 3.10 (2H, m); 2.22 (2H, m); 1.47 (3H, s).

EXAMPLE 17
The Synthesis of 2,2'-(4-iodo-1H-pyrazol-1,3-diyl)bis (pyridine) 1,1'-dioxide (19)

To a stirred solution of 2,2'-(1H-pyrazol-1,3-diyl)bis (pyridine) 1,1'-dioxide (9.9 g, 38.9 mmol) in conc. nitric acid/water 25 ml (1:1, v/v) iodine (9.8 g, 38.9 mmol) was added and the mixture was heated overnight at 95° C. The mixture was allowed to cool to room temperature and alkalized with 1 M NaOH. The aqueous layer was extracted three times with CHCl$_3$/EtOH (4:1), dried (Na$_2$SO$_4$) and concentrated. Purification on silica gel (eluent CH$_2$Cl$_2$:MeOH, 9:1, v/v) yielded 12.2 g (82%) of 19. $^1$H NMR δ (CDCl$_3$) 9.52 (1H., s); 8.37 (1H, m); 8.34 (1H, m); 8.09 (1H, m); 7.51 (1H, m); 7.41–7.30 (3H, m); 7.25 (1H, m).

EXAMPLE 18
The Synthesis of 6,6'-(4Iodo-1H-pyrazole-1,3-diyl)bis (pyridine)-2,2'-dicarbonitrile (20)

Trimethylsilyl cyanide (16.2 ml, 0.13 mol) was added to a mixture of 19 (4.92 g, 13.0 mmol) and CH$_2$Cl$_2$ (133 ml). After 5 min, benzoyl chloride (6 ml, 52 mmol) was added, and the mixture was stirred for 24 h at ambient temperature. The mixture was then concentrated (to ca. 15 ml), 10% K$_2$CO$_3$ solution (130 ml) was added and the mixture stirred for 2 h. A cold mixture was filtered, and the main product fraction was washed with water (50 ml) and cold CH$_2$Cl$_2$ (2×20 ml). The organic phase of filtrate was separated, and evaporated to dryness. A cooled mixture of the residue and diethyl ether (200 ml) was filtered. Total yield was 4.36 g (85%); IR (KBr) 2237 cm$^{-1}$ (C≡N), 1590, 1574 cm$^{-1}$ (arom.); $^1$H NMR δ (CDCl$_3$) 8.79 (1H., s); 8.30 (1H, dd, J 0.8 and 3.9); 8.34 (1H, dd, J 0.8 and 3.5); 8.02 (1H, dd, J7.5 and 8.5); 7.95 (1H, dd, J 7.7 and 8.1); 7.73 (1H, dd, J 1.0 and 7.7); 7.66 (1H, dd, J 0.8 and 7.5).

EXAMPLE 19
The Synthesis of tetramethyl 2,2',2",2"'-{[6,6'-(4-Iodo-1H-pyrazole-1,3-diyl)bis(pyridine)-2,2'-diyl]bis (methylenenitrilo)}tetrakis(acetate) (22)

A suspension of compound 20 (5.06 g, 12.7 mmol) and dry tetrahydrofuran (140 ml) was deaerated with nitrogen. Borane in tetrahydrofuran (1 M, 140 ml) was added within 10 min into the reaction mixture. After stirring for 24 h at room temperature, excess borane was destroyed by addition of MeOH, the mixture was evaporated and the residue dissolved in MeOH saturated with dry HCl (20 ml). After stirring for 1 h, the mixture was evaporated, and the residue treated with tetrahydrofuran (20 ml). The cooled mixture was filtered and the solid material washed with cold tetrahydrofuran (10 ml) and diethyl ether (5 ml). To give 7.47 g (94%) [ms (FAB$^+$) 407] of crude compound 21. A mixture of this material (3.1 g, 5.3 mmol), BrCH$_2$COOMe (2.0 ml, 21.1 mmol), dry N,N-diisopropylethylamine (13.8 ml, 79 mmol) and dry acetonitrile (110 ml) was refluxed for 24 h. After evaporation, the residue was dissolved in CHCl$_3$ (50 ml), washed with water (3×25 ml) and dried with Na$_2$SO$_4$. The product was purified by flash chromatography [silica gel, petroleum ether (40–60°)/ethyl acetate, 1:1]; yield 56% of compound 22. IR (film) 1732 cm$^{-1}$ (C═O), 1144 cm$^{-1}$ (C—O); $^1$H NMR δ (CDCl$_3$) 1.47 (18 H, s), 1.48 (18 H, s), 3.53 (4 H, s), 3.57 (8 H, s), 4.06 (2 H, s), 4.15 (2 H, s), 7.54 (1 H, d, J=7.6 Hz), 7.72 (1 H, d, J=8.0 Hz), 7.79 (1 H, t, J=7.6 Hz), 7.82 (1 H, t, J=8.0 Hz), 7.91 (1 H, d, J=7.6 Hz), 7.95(1 H, d, J=8.0 Hz), 8.70(1 H, s).

EXAMPLE 20

The Synthesis of tetramethyl 2,2',2",2'"-{{6,6'-(4-(5-hydroxyhexyn-1-yl)-1H-pyrazole-1,3-diyl)bis(pyridine)-2,2'-diyl}bis(methylenenitrilo)}tetrakis(acetate) (23)

A mixture of compound 22 (1.0 g, 1.44 mmol), 5-hexyn-1-ol (0.19 ml, 1.72 mmol), dry piperidine (4.5 ml) and dry DMF (6 ml) was deaerated with argon. Bis(triphenylphosphine)palladium(II) chloride (20 mg, 29 µmol) and copper iodide (11 mg, 58 µmol) was added and the mixture was stirred for 12 h at 40° C. After evaporation, the residue was dissolved in CHCl$_3$ (90 ml), washed with water (3×45 ml) and dried with Na$_2$SO$_4$. The product was purified by flash chromatography (eluent CH$_2$Cl$_2$:MeOH, 9:1). Yield, 0.90 g. [M+H[$^+$665.

EXAMPLE 21

The Synthesis of tetramethyl 2,2',2",2'"-{[6,6'-(4-(hexan-6-ol)-1H-pyrazole-1,3-diyl)bis(pyridine)-2,2'-diyl]bis(methylene-nitrilo)}tetrakis(acetate) (24)

A mixture of compound 23 (0.45 g, 0.68 mmol) 10% Pd on carbon (50 mg) and MeOH (30 ml) was stirred in a hydrogen atmosphere for 2.5 h. After filtration, the filtrate was evaporated and the residue was purified by flash chromatography (CH2CL2:MeOH, 9:1). The yield was 350 mg, 77%; ms 669 [M+H]$^+$

EXAMPLE 22

The Synthesis of the Non-nucleosidic phosphoramidite (25)

Compound 24 was phosphitylated using the method described in example 3. Yield after silica gel column chromatography (CH$_2$Cl$_2$:MeOH:TEA 9:1:1; v/v/v). $^{31}$P NMR (CDCl$_3$): 147.8.

EXAMPLE 23

The Synthesis of 5'-O-(4,4'-dimethoxytrityl)-N3-{tetramethyl-2,2',2",2'"-{6, 6'-[4'-hydroxyethoxyethoxyphenylethynyl]pyridine-2,6-diyl}bis(methylene-nitrilo)tetrakis(acetato)}thymidine 3'-succinate (26)

Compound 17 (0.67 mmol) was dissolved in dry pyridine (5 ml). Succinic anhydride (135 mg, 1.35 mmol) and cat. amount of DMAP were added, and the mixture was stirred overnight at room temperature and concentrated. The residue was dissolved in dichloromethane, washed with aqueous triethylamine and dried. Purification was performed on silica gel (eluent:10% MeOH in dichloromethane). Compound 26: $^1$H NMR (DMSO-d$_6$) δ 7.59 (1H, s); 7.54 (2H, d, J 8.8); 7.50 (2H, s); 7.38–7.21 (9H, DMTr); 7.00 (2H, d J 8.8); 6.90 (4H, d, DMTr); 6.27 (1H, dd); 5.31 (1H, m); 4.11 (3H, m); 4.02 (2H, m); 3.91 (4H, s); 3.79 (2H, m); 3.73 (8H, s); 3.61 (2H, m); 3.60 (12H, s); 3.37 (2H, m); 2.67 (2H, t); 2.42 (2H, t); 2.22 (2H, m); 1.47 (3H, s).

EXAMPLE 24

The Synthesis of the Solid Support (27)

Long chain alkylamine controlled pore glass was treated with a mixture of 10% TEA in 80% aqueous ethanol, washed with acetonitrile and dried. Compound 23 (0.5 mmol; as a pyridinium salt), N,N'-diisopropylcarbodiimide (1.0 mmol, 157 µl); and N-hydroxysuccinimide (0.5 mmol, 58 mg) was added to a suspension of the solid support in dry pyridine (5 ml) and the mixture was shaken overnight at ambient temperature. The suspension was filtered, washed with dry pyridine, kept in a mixture of Ac$_2$O:pyridine:N-methylimidazole (1:5:1; v/v/v) for 10 min, and finally washed with ether. Loading as judged on DMTr cation assay was 34 µmolg$^{-1}$.

EXAMPLE 25

The Synthesis of (E)-3-(4"Bromophenyl)-1-pyrid-2'-yl) prop-2-enone (28)

4-Bromobenzaldehyde (50 g, 0.27 mol) was added in the ice-cold mixture methanol (540 ml) and water (110 ml) containing potassium hydroxide (15.2 g). After all aldehyde was dissolved 2-acetylpyridine (30.3 ml, 0.27 mol) was added and the reaction was allowed to proceed overnight at ambient temperature. The precipitation formed was filtered, washed with cold methanol and dried. Yield was 64 g (82%).
$^1$H NMR (CDCl$_3$): δ 8.75 (1H, br. d); 8.31 (1H, d, J 12 Hz); 8.20 (1H, br d); 7.90 (1H, m); 7.87 (1H, d, J 12); 7.59 (5H, m). MS (EI+) 288, 289 [M+].

EXAMPLE 26

The synthesis of 4"-(4'"-bromophenyl)-2,2':6',2"-terpyridine (30)

A mixture of compound 28 (20.6 g, 71 mmol), dry ammonium acetate (137 g) and freshly prepared N-[2-(pyrid-2'-yl)-2-oxo-ethyl]pyridinium iodide (29; 23.3 g, 71 mmol) in dry methanol (650 ml) was heated at reflux overnight. The mixture was cooled to room temperature and refrigerated. The precipitation was separated by filtration, washed with cold methanol and dried. Yield was 12.5 g (45%). 1H NMR (dmso-d6) δ: 8.77 (2H, br d, J 4); 8.71 (2H, s); 8.69 (2H, d J 7.9); 8.06 (2H, td, J 2.5 and 7.5); 7.92 (2H, d, J 7.5); 7.79 (2H, d, J 7.5); 7.55 2H, m). MS (EI+) 388, 390 [M+].

EXAMPLE 27

The Synthesis of 4"-(4'"-Bromophenyl)-2,2':6',2"-terpyridine N,N"-Dioxide (31)

3-Chloroperbenzoic acid (29.1 g, 121 mmol) was added to compound 30 (12.4 g, 32 mmol) in dichloromethane (500 ml) and the mixture was stirred overnight at ambient temperature. The mixture was washed with 10% sodium carbonate (300 ml), dried (Na$_2$SO$_4$) and concentrated. Purification on silica gel (eluent 10% methanol in dichloromethane) gave 11.4 g (85%) of product. 1H NMR (dmso-d6) δ: 9.06 (2H, s); 8.43 (2H, m); 8.24 (2H, m); 7.80 (4H, s); 7.54 (4H, m). MS (EI+) 419, 421 [M+].

EXAMPLE 28

The Synthesis of 4"-(4'"-Bromophenyl)-2,2':6',2"-terpyridine-6,6"-dicarbonitrile (32)

Trimethylsilylcyanide (13.7 ml, 110 mmol) was added to compound 31 (4.6 g, 11 mmol) in dichloromethane (170 ml). After 5 min, benzoyl chloride (5.1 ml, 44 mmol) was added within 20 min. After stirring overnight, the mixture was evaporated to half volume, 10% solution of K$_2$CO$_3$ (100 ml) was added, the mixture was stirred for 15 min, and the precipitate filtered and washed with water and cold dichloromethane. Yield was 3.69 g (77%). 1H NMR (dmso-d6): δ 8.98 (2H, d, J 8.0); 8.68 (2H, s); 8.31 (2H, t, J 7.6); 8.21 (2H, d, J 7.6); 7.97 (2H, d, J 8.4); 7.80 (2H, d, J 8.4). IR (KBr): 2237 cm-1 (CN). MS (EI+)437, 439 [M+].

EXAMPLE 29

The Synthesis of tetramethyl 2,2',2",2'"-{[4'-(4"-bromophenyl)-2,2':6',2"-terpyridine-6,6"-diyl]bis(methylenenitrilo)}tetrakis (acetate) (34)

A suspension of compound 32 (3.65 g, 8.3 mmol) in dry THF (100 ml) was dearated with argon. BH$_3$. THF was added during 20 min. After stirring for 2.5 h at ice-bath, the excess of borane was destroyed by addition of methanol. The mixture was evaporated, and the residue was dissolved in methanol saturated with HCl (50 ml). After stirring for 2 h at room temperature, the mixture was concentrated. The residue was suspended in THF, filtered, washed with THF and dried. This material was suspended in dry DMF (50 ml). Diisopropylethylamine (21 ml), methyl bromoacetate (3.1 ml, 33.3 mmol) and KI (1.51 g, 9.1 mmol) were added, and the mixture was stirred overnight at room temperature and concentrated. The residue was dissolved in dichloromethane (80 ml), washed with sat NaHCO$_3$ (3·40 ml) and dried. Purification was performed on silica gel (eluent pet. ether:ethyl acetate:triethylamine 5:2:1, v/v/v) Yield was 6.6 g. 1H NMR (CDCl$_3$) δ: 8.68 (2H, s); 8.55 (2H, d, J 6); 7.87 (2H, t, J 6); 7.81 (2H, d, J 6); 7.68 (2H, d, J 6); 7.62 (2H, d, J 6); 4.19 (4H, s); 3.73 (8H, s); 3.70 (12H, s).

EXAMPLE 30
The Synthesis of tetramethyl 2,2',2",2'"-{[4'-(4"-(6-hydroxy-2-hexyn-1-yl)phenyl)-2,2':6',2"-terpyridine-6,6"-diyl]bis (methylenenitrilo)}tetrakis(acetate) (35)

Compound 34 (2.0 g, 2.72 mmol) and 5-hexyn-1-ol (360 ml; 3.28 mmol) were dissolved in the mixture of dry THF (15 ml) and triethylamine (4 ml) and the mixture was deaerated with argon for 10 min. Pd(Ph3P)2Cl2 (37.5 mg, 0.053 mmol) and CuI (21.9 mg, 0.11 mmol) were added and the mixture was stirred overnight at 60° C. The cooled mixture was filtered and the filtrate was concentrated in vacuo. The residue was dissolved in dichloromethane (50 ml), washed with water (2·20 ml) and dried. Purification on silica gel (eluent 10% methanol in dichloromethane (v/v)) gave 1.63 g (80%) of product. IR (film) 2232 cm$^{-1}$ (C≡C, weak). 1H NMR (CDCl$_3$) δ: 8.70 (2H, s); 8.55 (2H, d, J 7.9); 7.87 (2H, t, J 7.9); 7.85 (2H, d, J 8.6); 7.61 (2H, d, J 7.6); 7.56 (2H, d, J 8.2); 4.19 (4H, s); 3.73 (8H, s); 3.75 (2H, m); 3.70 (12H, s); 2.52 (2H, t, 6.7); 1.77 (6H, m); 1.74 (1H br). MS (FAB+) 752.

EXAMPLE 31
The Synthesis of 2'-deoxy-5'-O-(4,4'-dimethoxytrityl)-3-(2,2',2",2'"-{[4'-(4"-(5-hexyn-6-yl)phenyl)-2,2':6',2"-terpyridine-6,6"-diyl]bis(methylenenitrilo)}tetrakis(acetato) uridine (36)

2'-Deoxy-5'-O-(4,4'-dimethoxytrityl)uridine was allowed to react with compound 35 under Mitsunobu conditions as described for compound 1. Purification was performed on silica gel (eluent petr. ether: ethyl acetate: triethylamine; 2:5:1; v/v/v). Yield was 61%. 1H NMR (CDCl$_3$) δ: 8.70 (2H, s.); 8.55 (2H, d); 7.86 (4H, m); 7.76 (1H, d); 7.57 (4H, m); 7.37 (nH, d); 6.83 (4H, d); 6.37 (1H, t); 5.45 (1H, d); 4.59 (1H, m); 4.21 (4H, s); 4.09 (1H, m); 3.99 (2H, t); 3.79 (8H, s); 3.70 (12H, s); 3.49 (2H, m); 2.79 (1H, br s); 2.53 (2H, m and t); 2.29 (1H, m); 1.78 (4H, m).

EXAMPLE 32
The Synthesis of 2'-deoxy-5'-O-(4,4'-dimethoxytrityl)-3-6-{{4-[6,6"-bis[N,N-bis-(methoxycarbonylmethyl)aminomethyl]-2,2': 6',2"-terpyridine-4'-yl}phenyl}hex-5-yn-1-yl}uridine 3'-[O-(2-cyanoethyl)-N,N-diisopropyl]phosphoramidite (37)

Phosphitylation of compound 36 using the method described in Example 3 yielded the title compound after silica gel colum chlromatography as a white powder $^{31}$P NMR (CDCl$_3$): δ 148.7 (0.5 P), 148.3 (0.5 P).

EXAMPLE 33
6-{4-{6,6"-bis[N,N-bis(methoxycarbonylmethyl)aminomethyl]-2,2':6',2"-terpyridine-4'-yl}phenyl}hex-5-yn-1-ol [O-(2-cyanoethyl)-N,N-diisopropyl]-phosphoramidite (38).

Phosphitylation of compound 30 yielded the title compound as a Colorless oil (purified on silica gel) $^{31}$P NMR (CDCl3): δ 147.7 (1P).

EXAMPLE 34
Introduction of Primary Amino Groups to the Oligoncletide Structure with the Aid of Compound 3—Labeling of the Amino Groups with an europium(III) Chelate A model sequence d(TTCCTCCACTGT) was synthesized on an ABI instrument, and 5 phosphoramidites 3 were coupled to its 5'-terminus using standard conditions (concentration 0.1 M in acetonitrile, coupling time 30 s): No difference in coupling efficiency between 3 and normal nucleosidic building blocks were detected as judged on DMTr-cation response. After standard ammoniolytic deprotection, the oligonucleotide prepared was isolated on PAGE and desaltd on NAP columns. This oligonucleotide was finally labeled with the non-luminescent europium(III) chelate (39) as described in Dahlén, P., Liukkonen, L., Kwiatkowski, M., Hurskainen, P., Iitiä, A., Siitari, H., Ylikoski, J., Mukkala, V.-M., and Lövgren, T., Bioconjugate Chem., 1994, 5, 268.

EXAMPLE 35
Introduction of lanthanide(III) Chelates to the Oligonucletide Structure with the Aid of Compound 8

Model sequences were synthesized as described above in Example 34. One or 10 phosphoramidites 8 were coupled to its 5'-terminus using standard conditions. No difference in coupling efficiency between 8 and normal nucleosidic building blocks were detected. When the chain assembly was completed, the oligonucleotides were deprotected by first treating the solid support with 0.1 M sodium hydroxide for 4 h at ambient temperature. 1.0 M ammonium chloride was then added, and the solution was concentrated in vacuo. The residue was treated with conc. ammonia for 16 h at 60° C., after which europium citrate (10 eq. per ligand) was added, and the mixture was kept 90 min at room temperature. Desalting by NAP followed by RP HPLC yielded the desired oligonucleotide conjugates containing one or ten europium (III) chelates in their structure.

EXAMPLE 36
Introduction of a lanthanide(III) Chelate to the Oligonucleotide Structure with the Aid of Compound 38

The luminescent terpyridine chelate was introduced to the 5'-terminus of the oligonucleotide structure in the aid of blocks 38 analogously as described for block 8, except DMTr-On synthesis was applied.

SCHEME 1A

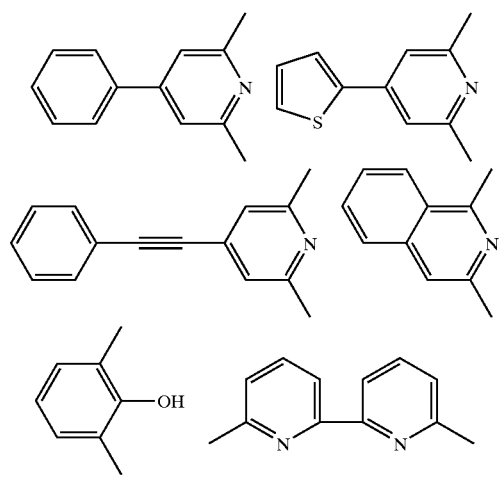

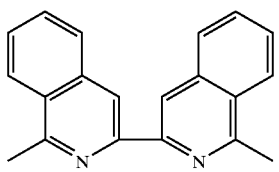
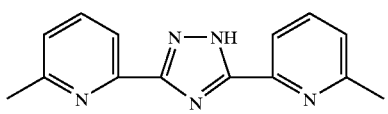
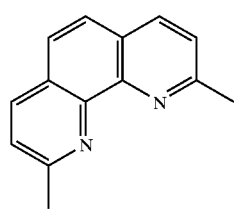
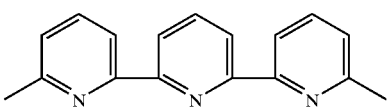
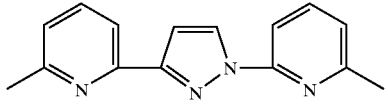
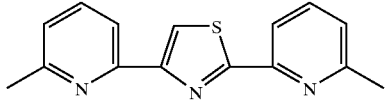
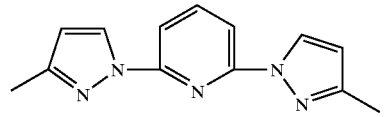
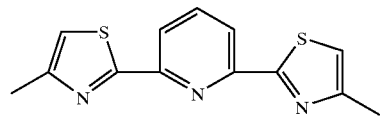
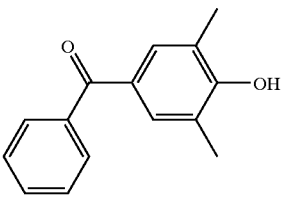
SCHEME 1B
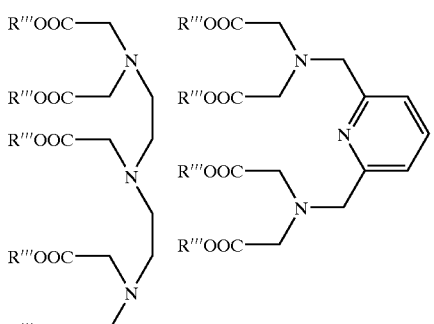
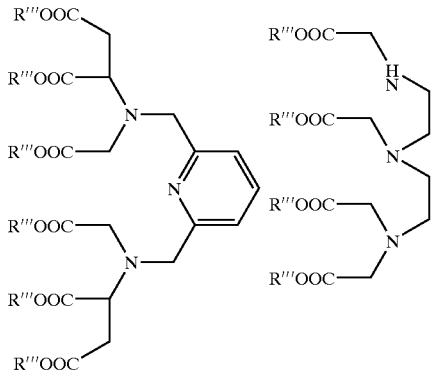
SCHEME 2
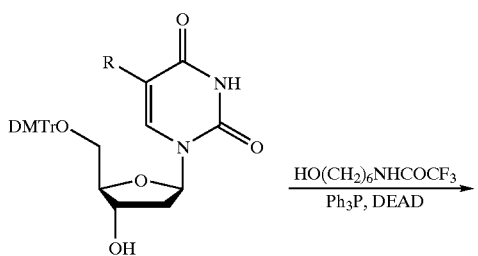

-continued
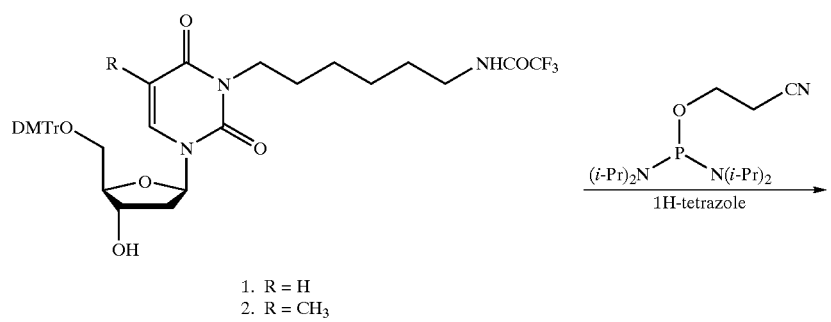
1. R = H
2. R = CH₃
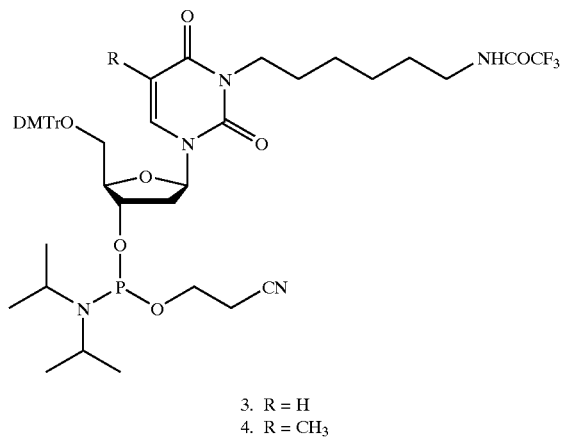
3. R = H
4. R = CH₃
SCHEME 3A
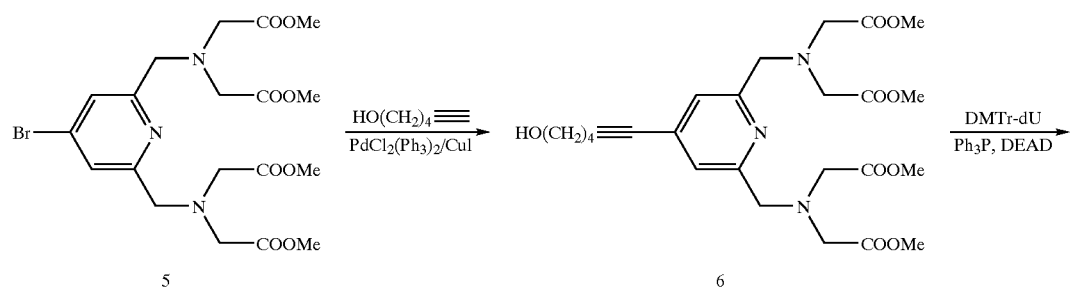
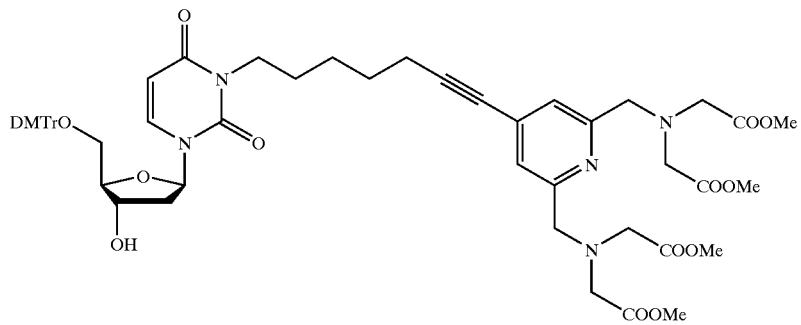

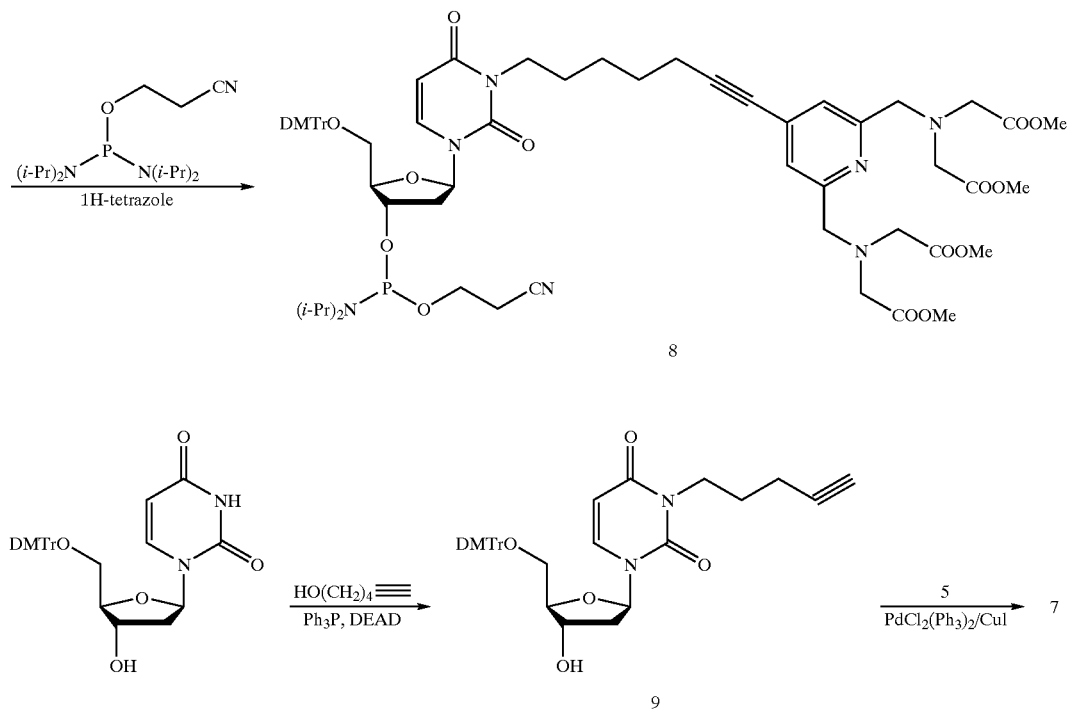
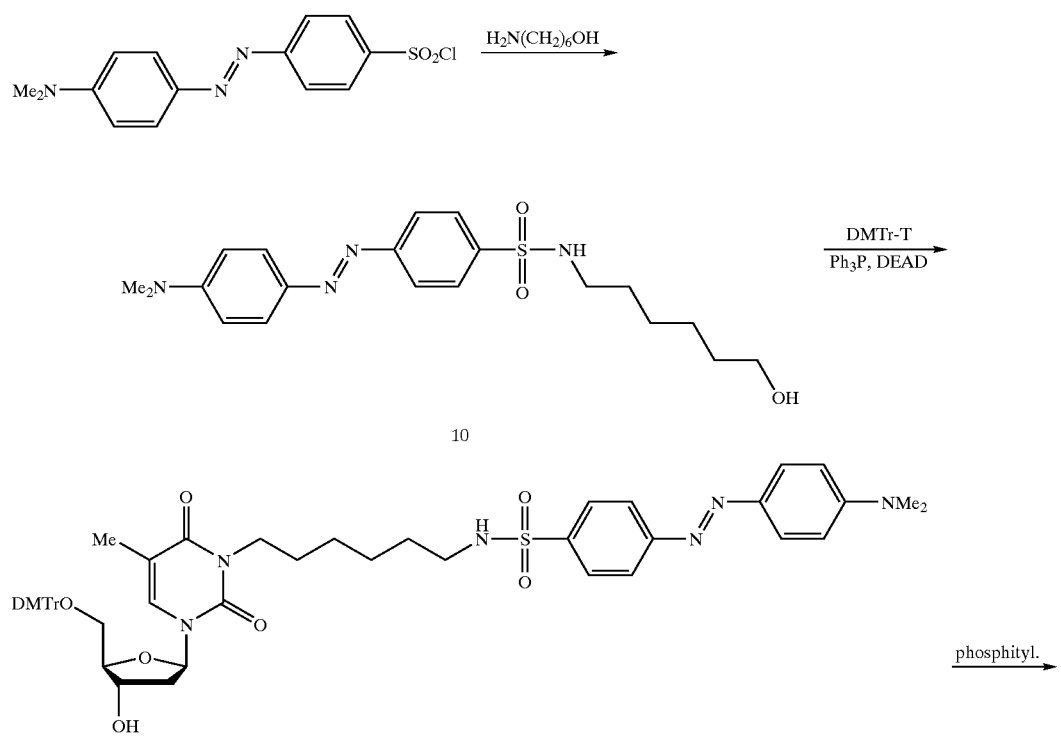

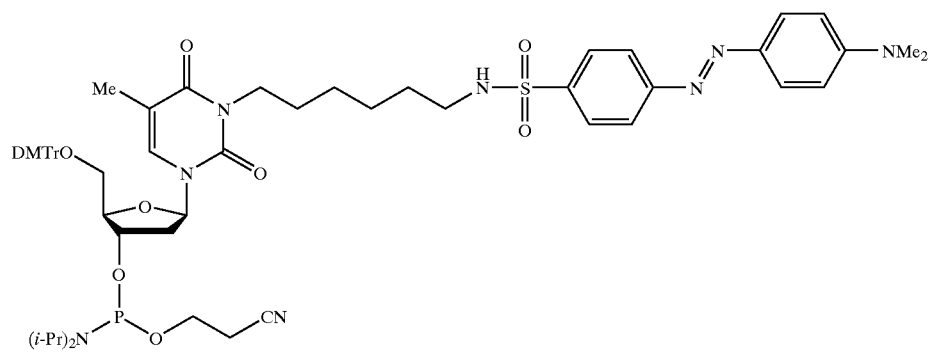
12
SCHEME 5A
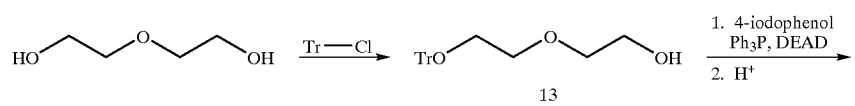
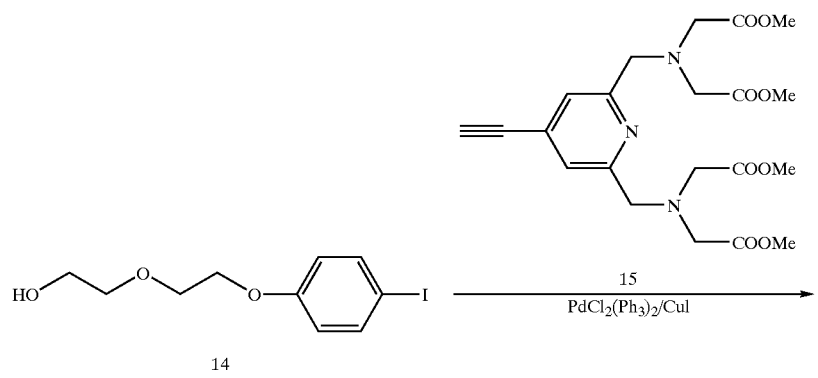
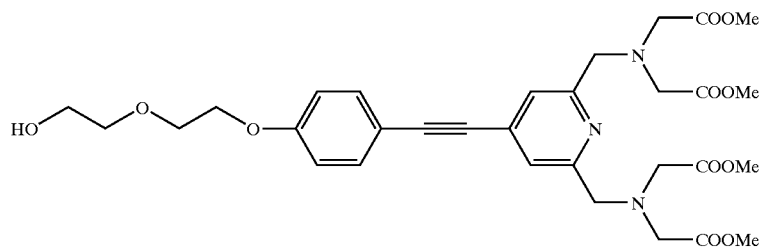
16

SCHEME 5B
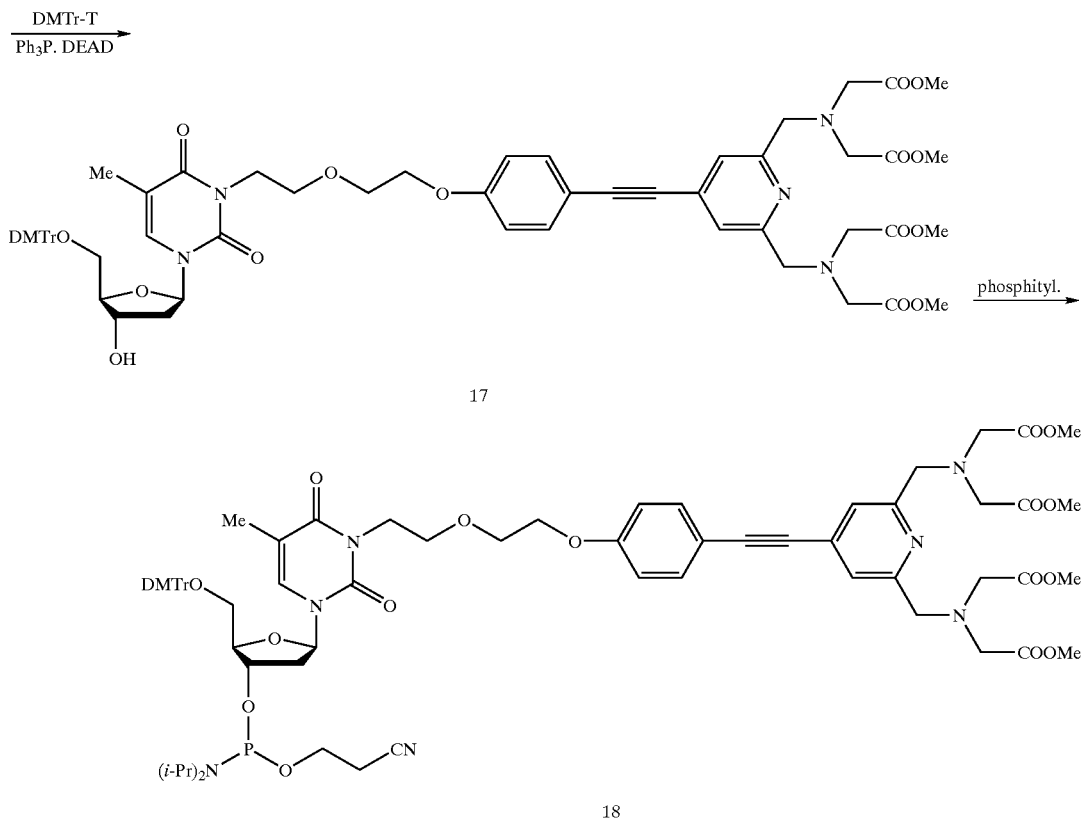
SCHEME 6A
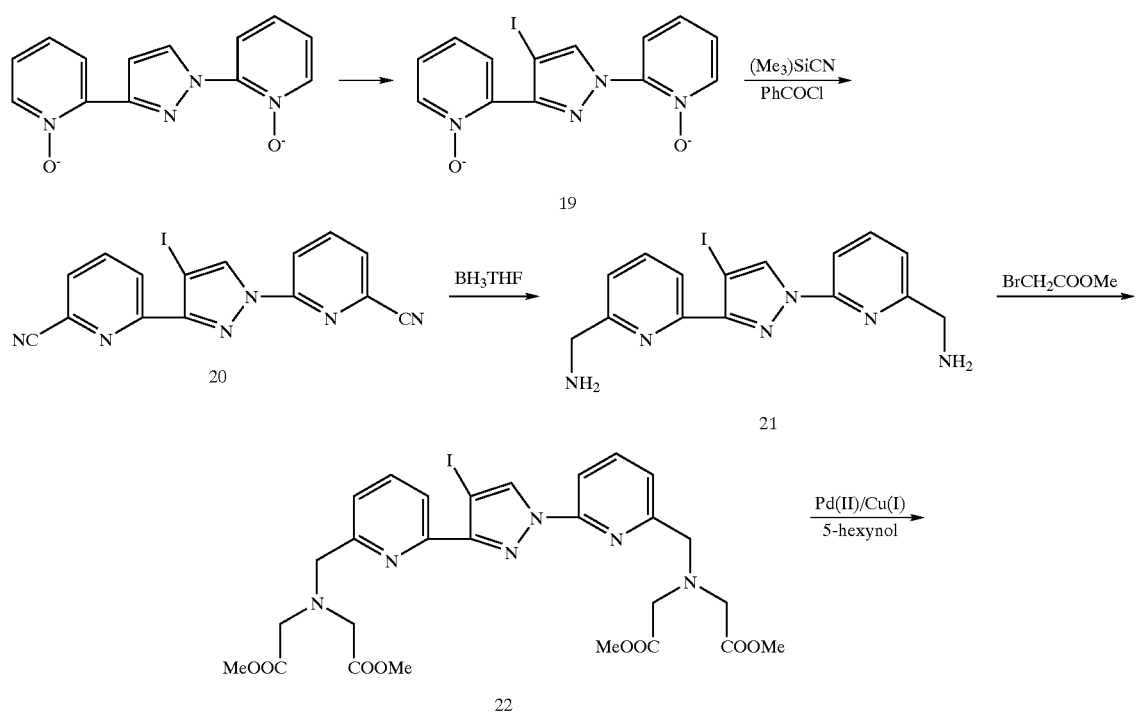

-continued
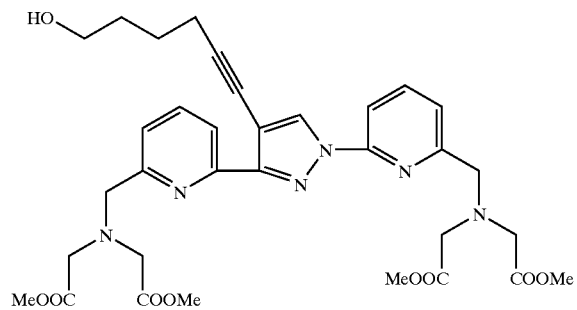
23
SCHEME 6B
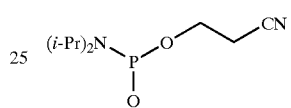
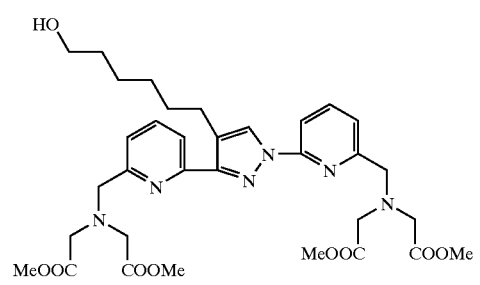
24
-continued
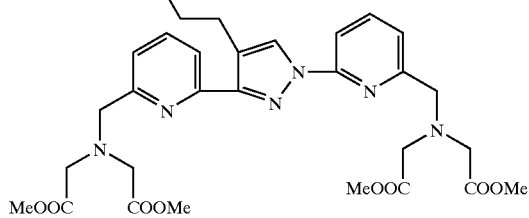
25
SCHEME 7A
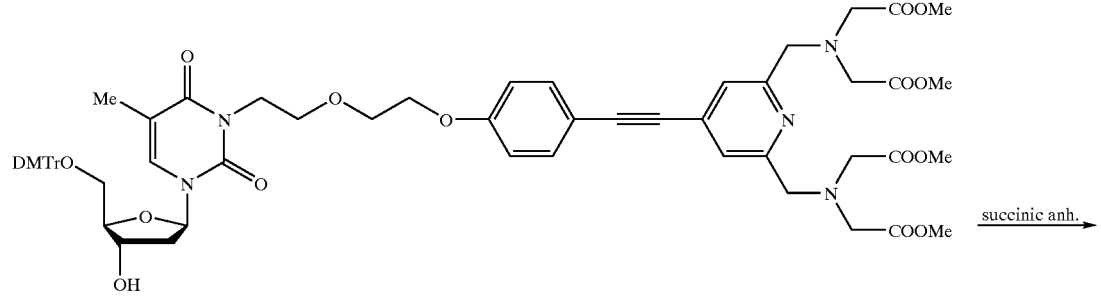
17

-continued
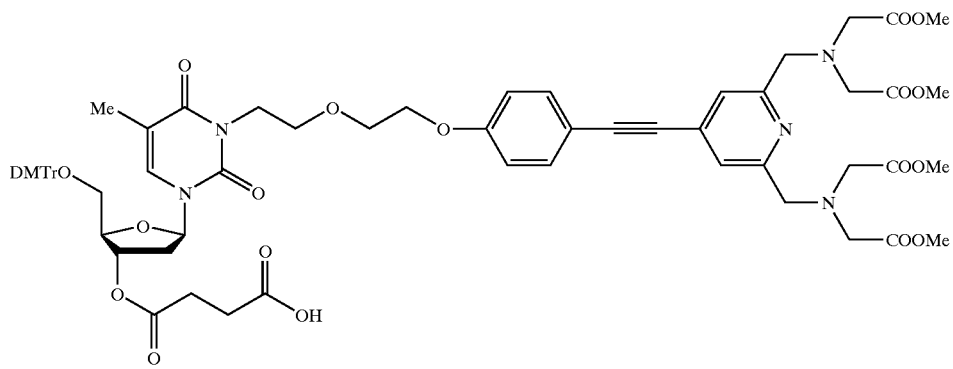
26
SCHEME 7B
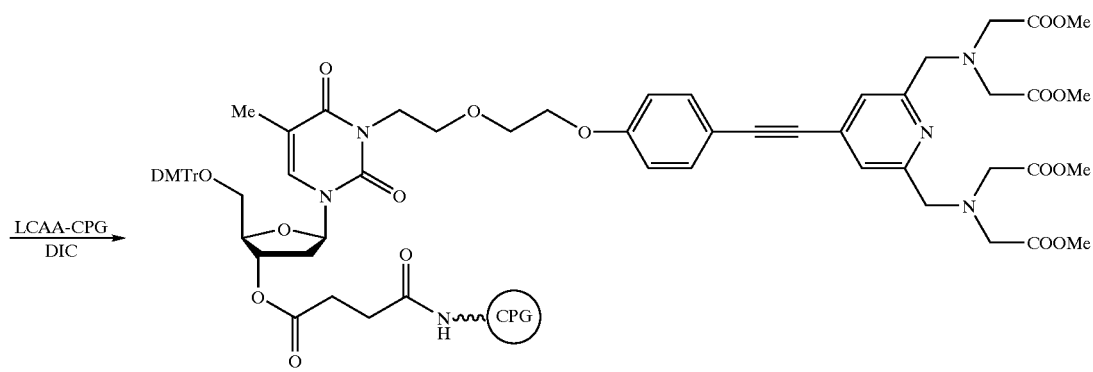
27
SCHEME 8A
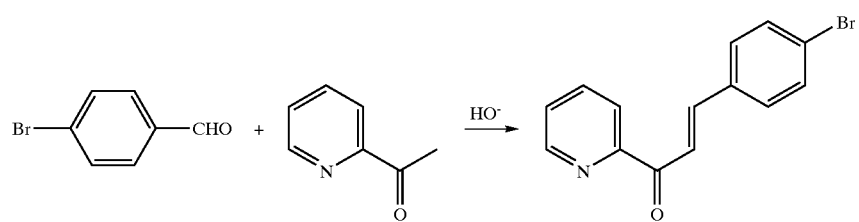
28
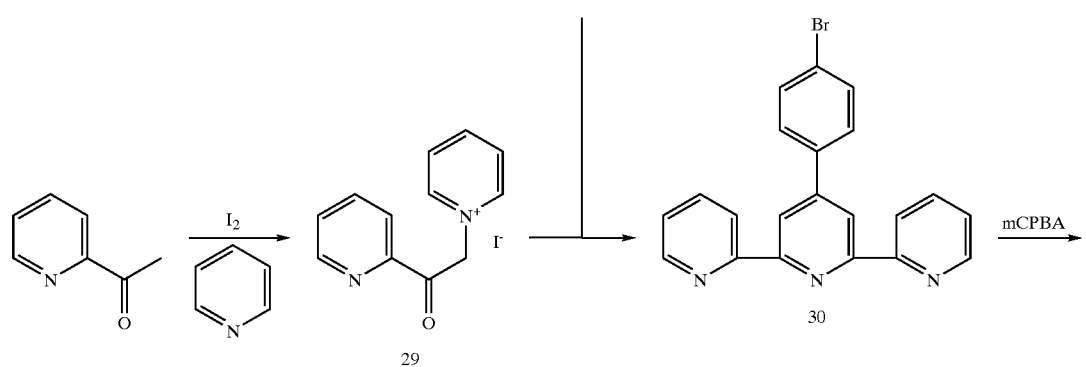
29 30

-continued
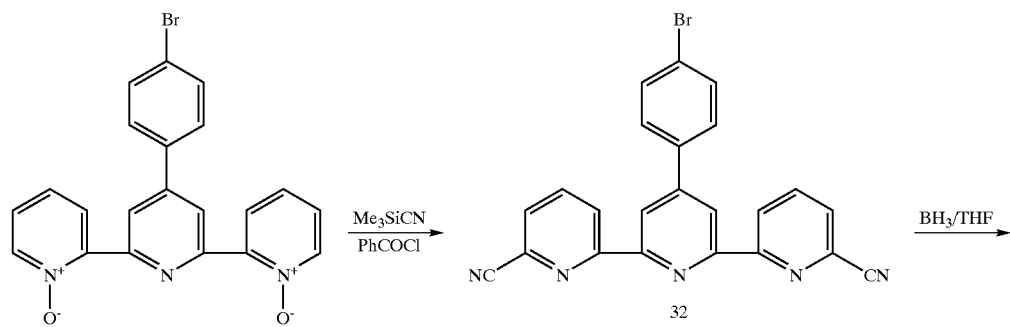
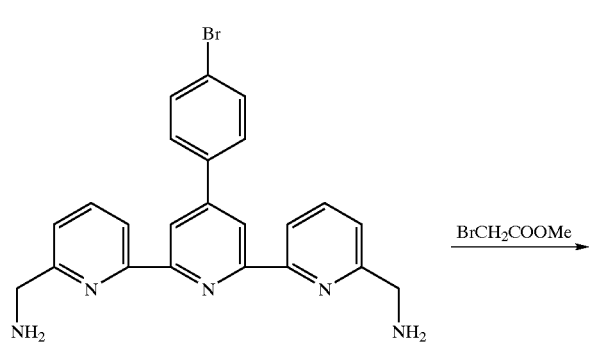
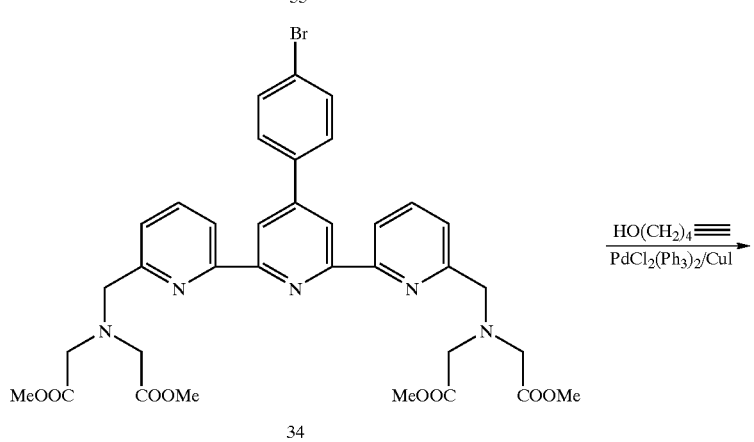
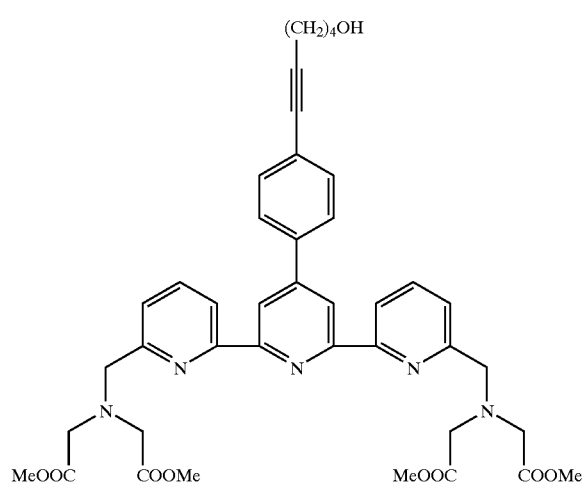

SCHEME 8B
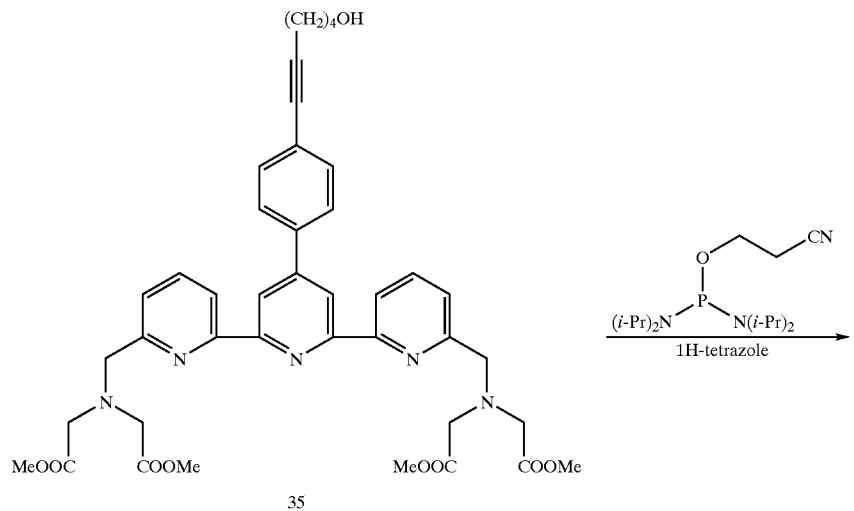
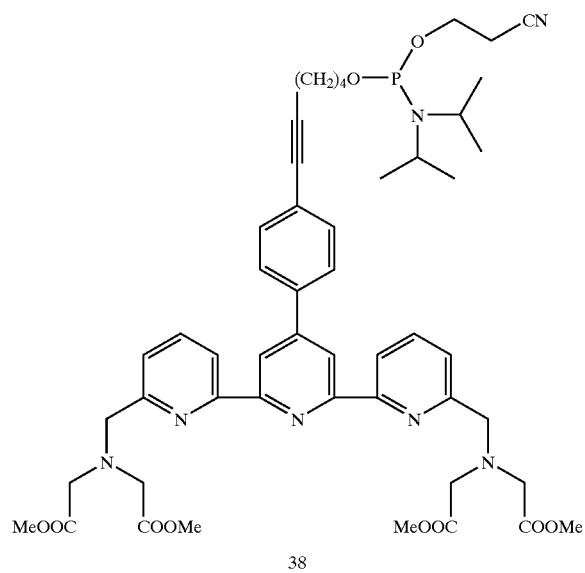
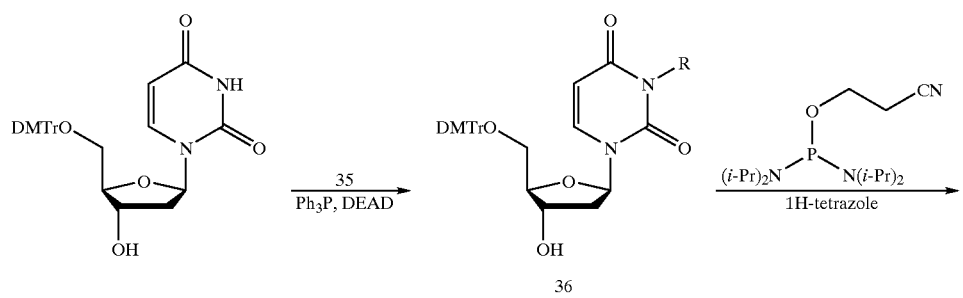

-continued
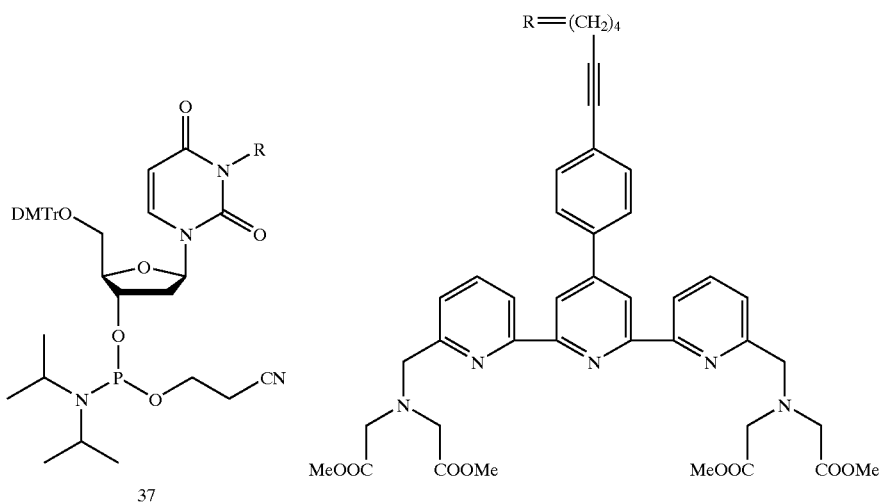
SCHEME 9
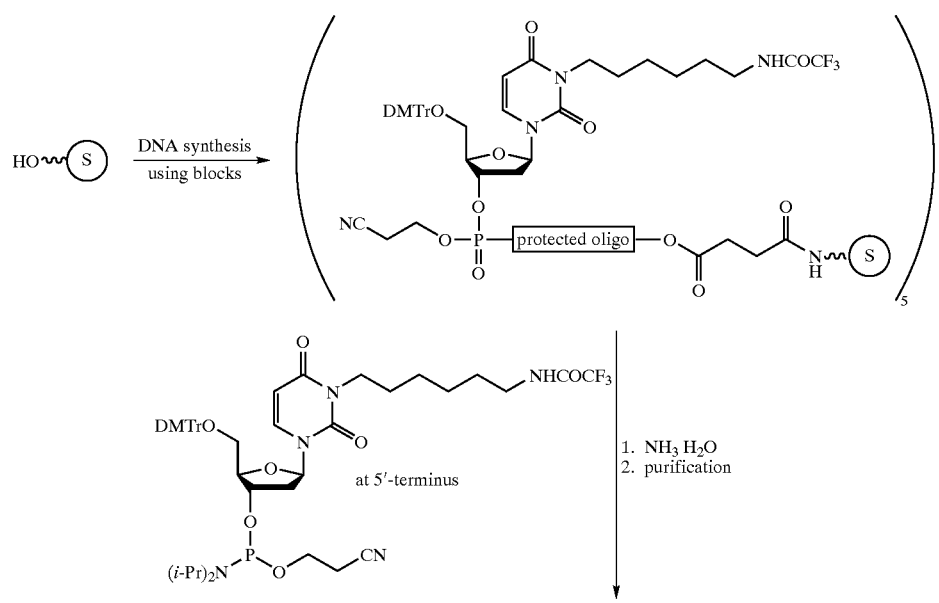

-continued
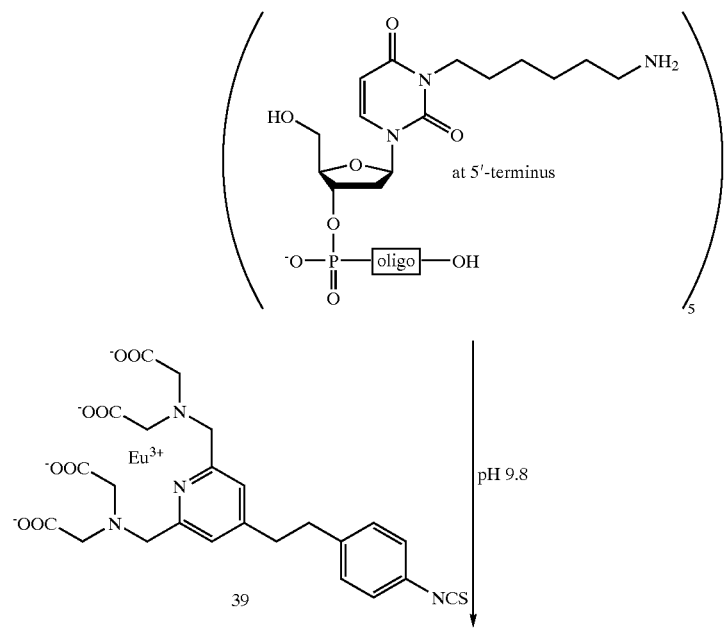
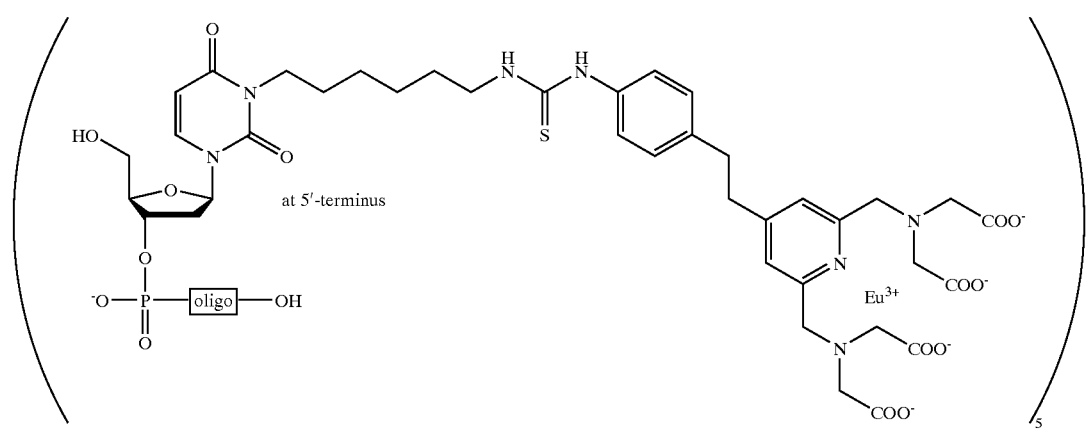

SCHEME 10
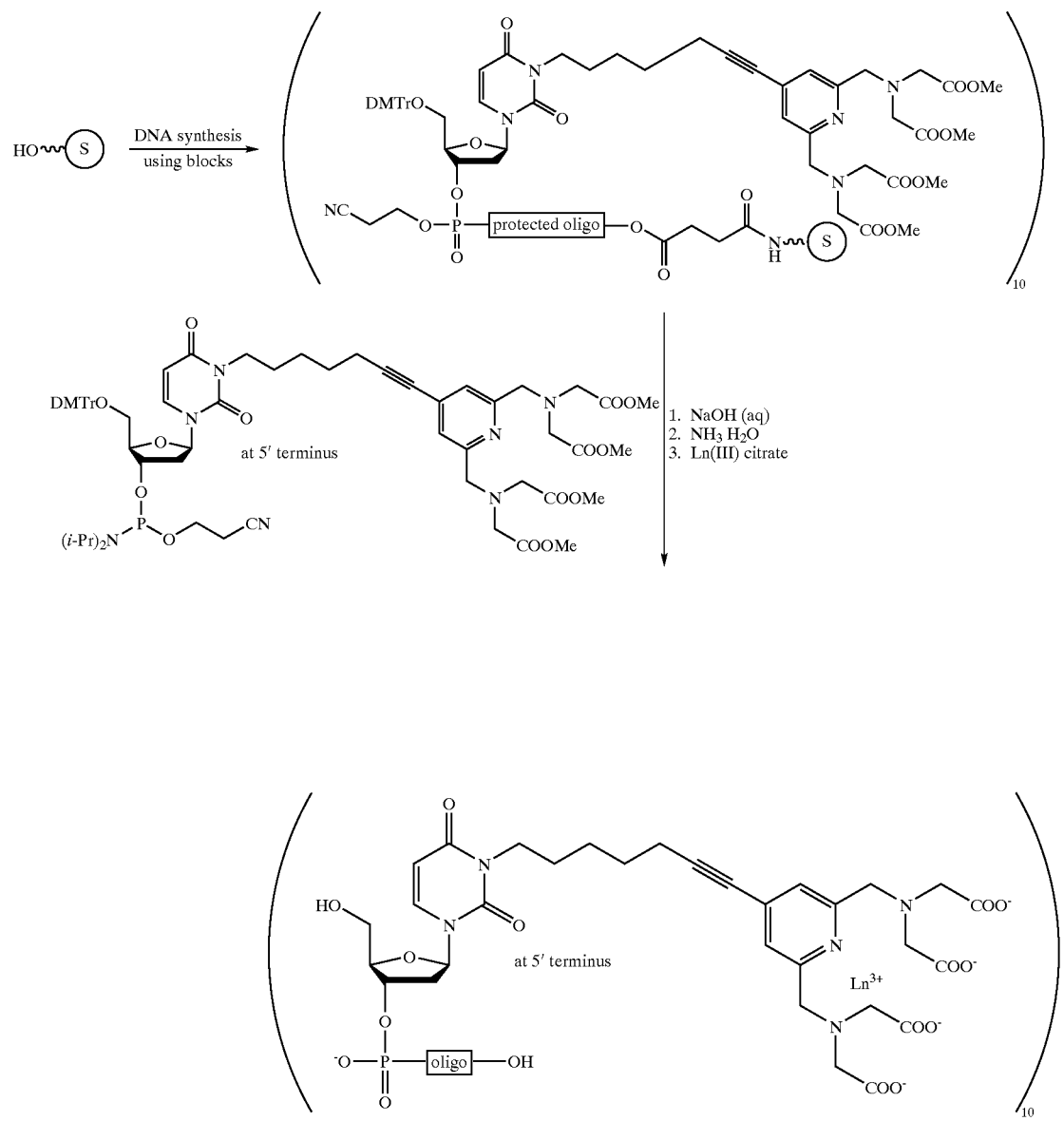
SCHEME 11
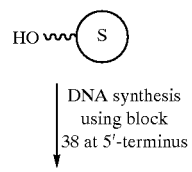

-continued
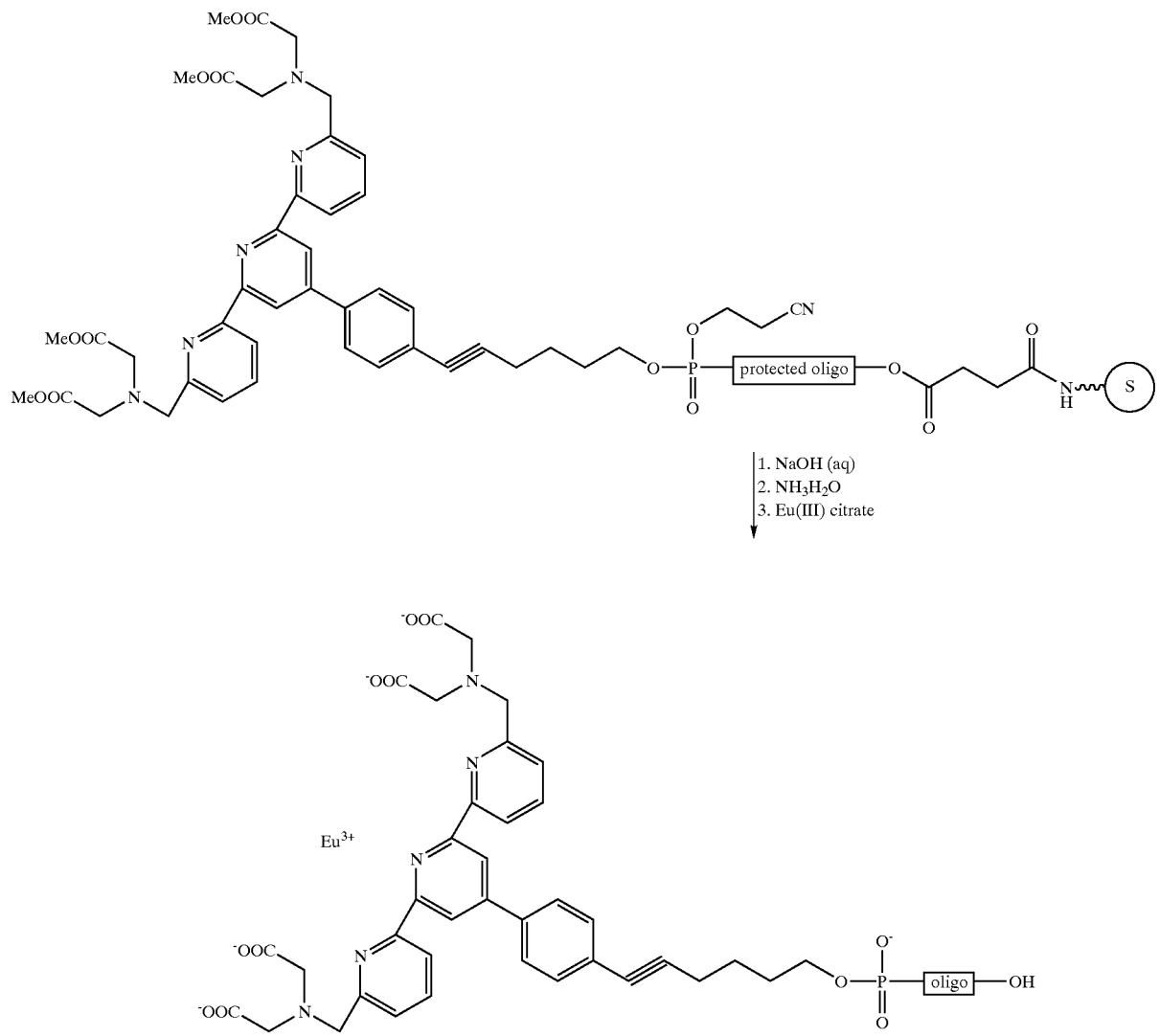

What is claimed is:

1. A labeling reactant of formula (I) suitable for labeling an oligonucleotide $$R-Z-A \quad \text{with } E' \text{ and } G \text{ substituents on } Z \tag{I}$$

wherein
R is a protecting group or is hydrogen;
A is either a phosphorylating moiety $$-O-\underset{L'}{\overset{L}{\underset{\|}{P}}}-L''$$

where
L is O, S, or is not present
L' is H, L'''CH$_2$CH$_2$CN or L'''Ar, where Ar is phenyl or its substituted derivative, where the substituent is nitro or chlorine, and L''' is O or S;
L'' is O$^-$, S$^-$, Cl, N(i-Pr)$_2$; or
A is a solid support tethered to Z via a linker arm, which is formed of one to ten moieties, each moiety being selected from a group consisting of phenylene, alkylene containing 1–12 carbon atoms, ethynediyl, ether, thioether, amide, carbonyl, ester, disulfide, diaza, and tertiary amine;
Z is a bridge point and is formed from

[three pyrimidine nucleoside structures with X, E'—G, R—O—, R'' substituents]

where
R'' is H or X'X'', where
X' is —O—, —S—, —N—, ON— or —NH— and X'' is a protection group or
X' is —O— and X'' is alkyl or alkoxyalkyl;
X is H, alkyl, alkynyl, allyl, Cl, Br, I, F, S, O, NHCOCH(CH$_3$)$_2$, NHCOCH$_3$, NHCOPh, SPh$_3$, OCOCH$_3$ or OCOPh;
E' is a linker arm between G and Z, bonded to Z at nitrogen in the pyrimidyl ring and is formed of one to ten moieties, each moiety being selected from the group consisting of phenylene, alkylene containing 1–12 carbon atoms, ethynediyl, ether, thioether, amide, carbonyl, ester, disulfide, diaza, and tertiary amine, or is not present;
G is a bivalent aromatic structure, tethered to two iminodiacetic acid ester groups N(CH$_2$COOR''')$_2$ where
R''' is an alkyl of 1 to 4 carbon atoms, allyl, ethyltrimethylsilyl, phenyl or benzyl, and
said bivalent aromatic structure is capable of absorbing light or energy and transferring the excitation energy to a lanthanide ion after the solid phase synthesis made labeling reactant has been released from the used solid support, deprotected and converted to a lanthanide chelate, or
G is a structure selected from a group consisting of

[four chelator structures with R'''OOC groups, pyridine and amine backbones]

where
R''' is an alkyl of 1 to 4 carbon atoms, allyl, ethyltrimethylsilyl, phenyl or benzyl, and
one of the hydrogen atoms is substituted with E', or
G is a protected functional group, where the functional group is amino, aminooxy, carboxyl, thiol, and the protecting group is pthaloyl, trityl, 2-(4-nitrophenylsulfonyl)ethoxycarbonyl, fluorenylmethyloxycarbonyl, benzyloxycarbonyl, trifluoroacetyl or t-butoxycarbonyl for amino and aminooxy, alkyl for carbonyl and alkyl or trityl for thiol.

2. The labeling reactant of claim 1, wherein R is a member of the group consisting of 4,4'dimethoxytrityl, 4-methoxytrityl, trityl, and (9-phenyl)xanthen-9-yl.

3. The labeling reactant of claim 1, wherein X'' is a member of the group consisting of t-butyldimethylsilyl-, tetrahydropyranyl, 1-(2-fluorophenyl)-4-methoxypiperidin-4-yl-, 1-(2-chloro-4-methyl)phenyl]-4-metoxypiperidin-4-yl-, 4-methoxytetrahydropyran-4-yl-, phthaloyl-, acetyl, pivaloyl-, benzoyl-, 4-methylbenzoyl, benzyl-, and trityl.

4. The labeling reactant of claim 1, wherein G is a protected functional group.

5. The labeling reactant of claim 4, wherein said protected functional group is selected from the group consisting of amino, carboxyl, aminooxy and thiol.

6. The labeling reactant of claim 1, wherein G is an organic dye.

7. The labeling reactant of claim 6, wherein said organic dye is selected from the group consisting of dabsyl, dansyl, fluorescein, rhodamine and tetramethyl-6-carboxyrhodamine (TAMRA).

8. The labeling reactant of claim 1, wherein the temporary protecting group R is 4,4'-dimethoxytrityl.

9. The labeling reactant of claim 1, wherein said reactant is a nucleotide and the sugar of the nucleotide is 2-deoxyribose or 3-deoxyribose.

10. The labeling reactant of claim 9, wherein X' is hydroxyl.

11. The labeling reactant of claim 10, wherein the permanent protection group X" of X' is selected from the group consisting of t-butyldimethylsilyl, tetrahydropyranyl, 1-(2-fluorophenyl)-4-methoxypiperidin-4-yl-, 1-[2-chloro-4-methyl)phenyl]-4-methoxypiperidin-4-yl- and 4-methoxytetrahydropyran-4-yl-.

12. The labeling reactant of claim 11, wherein X" is an alkyl or alkoxyalkyl.

13. The labeling reactant of claim 12, wherein X" is selected from the group consisting of methyl, methoxymethyl and ethoxymethyl.

14. The labeling reactant of claim 1, wherein G is a bivalent aromatic structure.

15. The labeling reactant of claim 14, wherein G is selected from the group consisting of

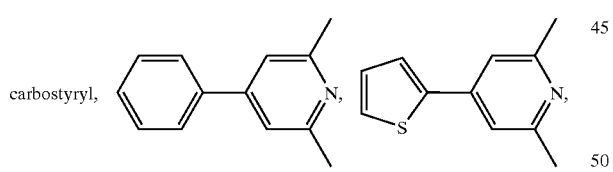

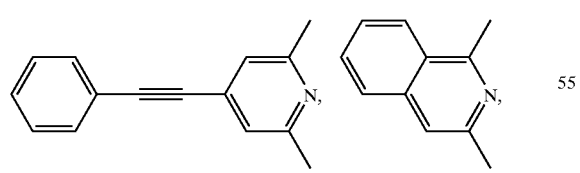

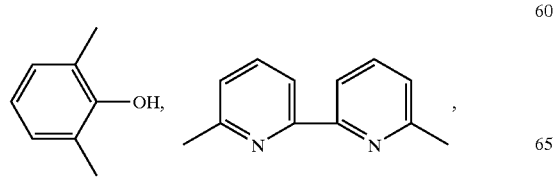

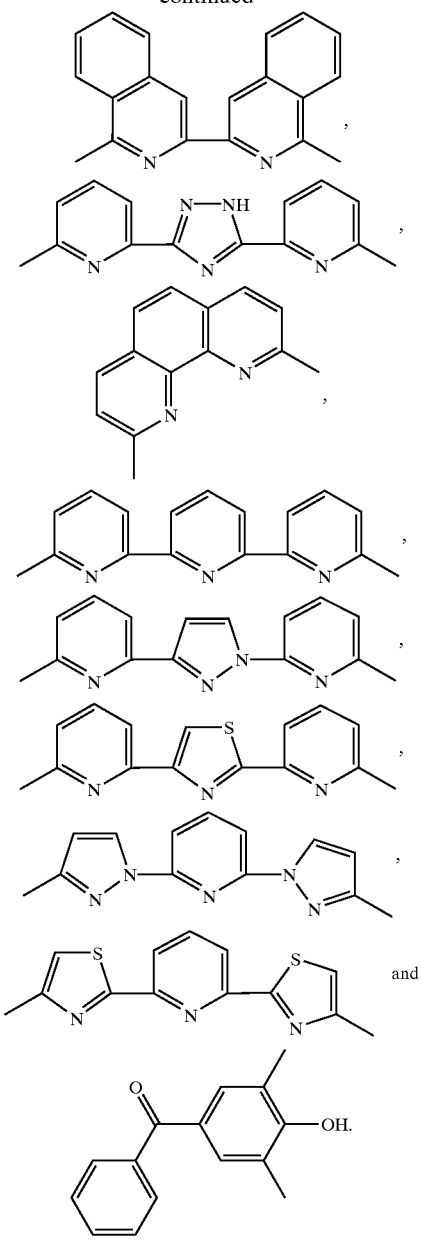

16. The labeling reactant of claim 1, wherein said reactant is non-luminescent and G is selected from a group consisting of

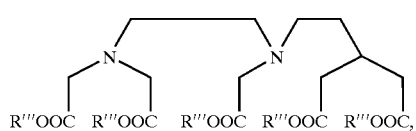

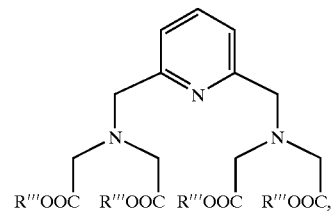

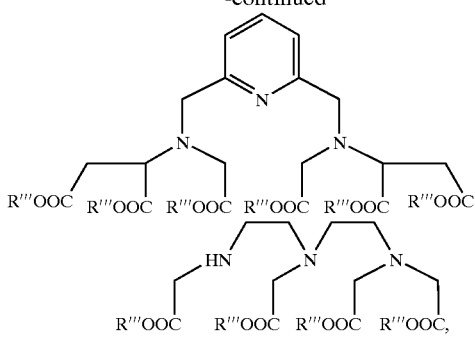

and wherein

R''' is an alkyl of 1 to 4 carbon atoms, allyl, ethyltrimethylsilyl, phenyl or benzyl, which phenyl or benzyl can be substituted or unsubstituted, and one of the hydrogen atoms is substituted with E'.

17. The labeling reactant of claim 16, wherein R''' is selected from the group consisting of methyl, ethyl and allyl.

18. The labeling reactant of claim 1, wherein the labeling reactant is selected from the group consisting of 2'-deoxy-5'-O-(4,4'-dimethoxytrityl)-N3 (tetramethyl 2,2', 2",2'''-[(4-(1-hexyn-5-yl )pyridine-2,6 -diyl)bis (methylennenitrilo)}tetrakis(acetato)uridine 3'-O-(2-cyanoethyl N,N-diisopropyl)phosphoramidite, N3-[6-[4-(dimethylamino)azobenzene-4'-sulfonamido] hex-1-yl-5'-O-(4,4'-dimethoxytrityl)thymidine 3'-O-(2-cyanoethyl N,N-diisopropyl)phosphoramidite, 5'-O-(4,4'-dimethoxytrityl)-N3-{tetramethyl-2,2',2",2'''-(6,6'-[4'-hydroxyethoxyethoxyphenylethynyl]pyridine-2,6-diyl)bis(methylenenitrilo)tetrakis(acetato) }thymidine3'-O-(2-cyanoethyl N,N-diisopropyl) phosphoramidite, and 2'-deoxy-5'-O-(4,4'-dimethoxytrityl)-3-6-{{4-{6,6"-bis [N,N-bis(methoxycarbonylmethyl)aminomethyl]-2, 2':6',2"-terpyridine-4'-yl}phenyl}hex-5-yn-1-yl}uridine 3'-[O-(2-cyanoethyl)-N,N-diisopropyl] phosphoramidite.

* * * * *

UNITED STATES PATENT AND TRADEMARK OFFICE
CERTIFICATE OF CORRECTION

PATENT NO.        : 6,949,639 B1
APPLICATION NO. : 09/847384
DATED             : September 27, 2005
INVENTOR(S)       : Jari Hovinen and Harri Takalo It is certified that error appears in the above-identified patent and that said Letters Patent is hereby corrected as shown below:

IN THE ABSTRACT:

Change the first G structure to 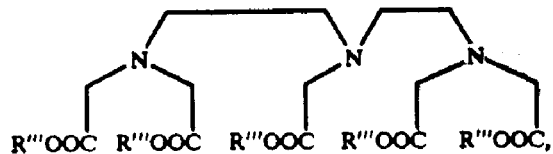

IN THE SPECIFICATION:

Col. 4, change formula I to 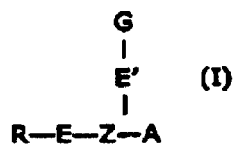

Col. 6, change the first G structure to 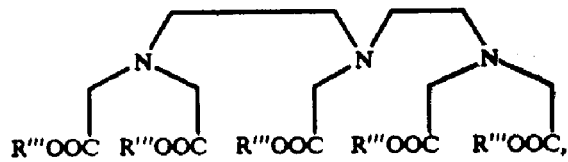

Col. 10, line 11, change "provided" to --produced--.

UNITED STATES PATENT AND TRADEMARK OFFICE
CERTIFICATE OF CORRECTION

PATENT NO.       : 6,949,639 B1
APPLICATION NO.  : 09/847384
DATED            : September 27, 2005
INVENTOR(S)      : Jari Hovinen and Harri Takalo It is certified that error appears in the above-identified patent and that said Letters Patent is hereby corrected as shown below:

IN THE CLAIMS:

Claim 1, Col. 50, change the first G structure to

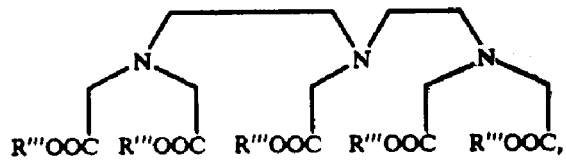

Claim 12, Col. 51, line 34, change "claim 11" to --claim 9--.

Claim 16, Col. 52, change the first G structure to

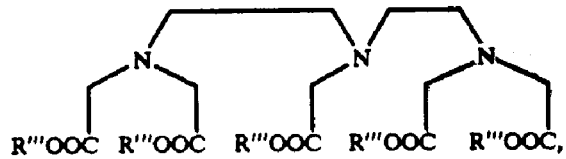

Signed and Sealed this

Seventeenth Day of October, 2006

JON W. DUDAS
*Director of the United States Patent and Trademark Office*